United States Patent
Pan

(10) Patent No.: US 7,556,942 B2
(45) Date of Patent: Jul. 7, 2009

(54) TUMOR SUPPRESSOR DESIGNATED HIPPO

(75) Inventor: Duojia Pan, Baltimore, MD (US)

(73) Assignee: Board of Regents, The University of Texas System, Austin, TX (US)

(*) Notice: Subject to any disclaimer, the term of this patent is extended or adjusted under 35 U.S.C. 154(b) by 566 days.

(21) Appl. No.: 10/892,544

(22) Filed: Jul. 15, 2004

(65) Prior Publication Data

US 2005/0053592 A1    Mar. 10, 2005

Related U.S. Application Data

(60) Provisional application No. 60/487,511, filed on Jul. 15, 2003.

(51) Int. Cl.
*C12P 21/04* (2006.01)
*C12P 21/06* (2006.01)

(52) U.S. Cl. .................. 435/70.1; 435/69.1

(58) Field of Classification Search .......... 536/23.2, 536/23.1; 435/194, 252.3, 320.1, 6, 69.1, 435/70.1
See application file for complete search history.

(56) References Cited

U.S. PATENT DOCUMENTS 5,837,694 A * 11/1998 Barrett .................. 514/44
6,500,938 B1   12/2002 Au-Young et al. ........ 536/23.1
6,846,970 B1 *  1/2005 Christou et al. .......... 800/293

FOREIGN PATENT DOCUMENTS

WO    01/71042   *  9/2001

OTHER PUBLICATIONS

GenEmbl Database, Accession No. AY069088, Dec. 2001.*
Geneseq Database, accession No. ABK54776, Jun. 2002.*
Smith et al., Restorative Neurology and Neuroscience, 8, 21-34, 1995.*
Wikipedia search of Hela cells, Jul. 2008.*
Harvey et al., "The Drosophila mst ortholog, hippo, restricts growth and cell proliferation and promotes apoptosis,", Cell, 2003.
Justice et al., "The Drosophila tumor suppressor gene warts encodes a homolog of human myotonic dystrophy kinase and is required for the control of cell shape and proliferation," *Genes Dev.*, 9:534-546, 1995.
Kango-Singh et al., "Shar-pei mediates cell proliferation arrest during imaginal disc growth in Drosophila," *Development*, 129:5719-5730, 2002.
Tapon et al., "salvador promotes both cell cycle exit and apoptosis in Drosophila and is mutated in human cancer cell lines," *Cell*, 110:467-478, 2002.
Wu et al., "hippo encodes a ste-20 family protein kinase that restricts cell proliferation and promotes apoptosis in conjuction with salvador and warts," *Cell*, Jul. 15, 2003.
Xu et al., "Identifying tumor suppressors in genetic mosaics: the Drosophila lats gene encodes a putative protein kinase," *Development*, 121:1053-1063, 1995.

* cited by examiner

*Primary Examiner*—Maryam Monshipouri
(74) *Attorney, Agent, or Firm*—Fulbright & Jaworski, LLP

(57) ABSTRACT

Tumor suppressor genes (TSGs) play a major role in the pathogenesis of human cancers. Here, a new TSG designated hippo (hpo) is described, and the human homolog mst2 is identified as an additional TSG. hpo as a gene that regulates both cell proliferation and cell death in *Drosophila*, and encodes a Ste-20 family protein kinase that binds to and phosphorylates the tumor suppressor protein Salvador (Sav), which is known to interact with the Warts (Wts) protein kinase. Loss of hpo results in elevated transcription of the cell cycle regulator cyclin E and the cell-death inhibitor diap1, leading to increased proliferation and reduced apoptosis. Further, hpo, sav, and wts define a pathway that regulates diap1 at the transcriptional level. A human homolog of hpo completely rescues the overgrowth phenotype of *Drosophila* hpo⁻ mutants.

8 Claims, 8 Drawing Sheets

TUMOR SUPPRESSOR DESIGNATED HIPPO

The instant application claims benefit of priority to U.S. Provisional Ser. No. 60/487,511, filed Jul. 15, 2003, the entire contents of which are hereby incorporated by reference.

This invention was made with government support under grant No. GM 62323 awarded by the National Institutes of Health. The government has certain rights in the invention.

BACKGROUND OF THE INVENTION

1. Field of the Invention

The invention generally relates to the fields of molecular biology and oncology. More specifically, it relates to the identification of a new tumor suppressor gene (TSG) designated hippo and the corresponding polypeptide. Uses for hippo in diagnosis and therapy of cancer are provided.

2. Related Art

During metazoan development, cell-intrinsic and -extrinsic factors act coordinately to specify the characteristic size and number of diverse cell types (Conlon and Raff, 1999; Stocker and Hafen, 2000). The final number of cells in an organ or organism is determined by the balanced act of cell proliferation and cell death (apoptosis). A challenge is to understand how these processes are coordinated in normal development and how aberrant regulation of this coordination leads to pathological conditions such as cancer.

The relationships between cell proliferation and cell death are complex. It has long been observed that increased proliferation due to activation of oncogenes such as Myc or Ras is often accompanied by increased apoptosis (reviewed in Green and Evan, 2002). This has led to the proposal that apoptosis act as a built-in failsafe to prevent "inappropriate" proliferation of somatic cells (Green and Evan, 2002). Thus, sustained growth of cancer cells not only requires activation of the cell proliferation machinery, but also suppression of the apoptotic failsafe mechanisms. In most cases, this is brought about by coupling oncogene activation with antiapoptotic lesions such as overexpression of Bcl-2 or loss of p53 (Green and Evan, 2002). However, it is also possible that there exist gene networks that couple proliferation to apoptosis in such a manner that loss of a single gene may simultaneously promote proliferation and suppress apoptosis.

The compound eye of *Drosophila* provides an excellent model to decipher the mechanisms that coordinate cell proliferation and apoptosis. This highly organized structure develops from the eye imaginal disc wherein cell proliferation and apoptosis occurs in a stereotyped manner (Wolff and Ready, 1993). Cells divide asynchronously during early larval periods. Starting in the mid-third instar larval stage, a morphogenetic furrow (MF) moves across the eye imaginal disc from posterior to anterior. Cells anterior to the MF are undifferentiated and divide asynchronously, whereas cells in the MF are synchronized in the G1 phase of the cell cycle. Posterior to the MF, cells either exit the cell cycle and differentiate or undergo one round of synchronous division (second mitotic wave, SMW) before differentiation. These cells assemble into approximately 750 ommatidia, leaving behind approximately 2000 superfluous cells that are eliminated by a wave of apoptosis ~36 hr after puparium formation (APF) (Wolff and Ready, 1993).

Previous studies have identified cyclin E (CycE) and DIAP1 as key regulators of cell cycle and apoptosis, respectively (Richardson et al., 1995; Hay et al., 1995). Cell cycle exit requires the downregulation of CycE/cdk2 activity, while DIAP1 functions by inhibiting the proapoptotic caspases. That coordinated regulation of cyclin E and DIAP1 might play a critical role organ size control is supported by recent studies of the *Drosophila* tumor suppressor gene salvador (sav, also called shrp), which encodes a protein containing WW and coiled-coil domains (Tapon et al., 2002; Kango-Singh et al., 2002). Loss of sav leads to increased cell proliferation and decreased apoptosis associated with elevated levels of CycE and DIAP1 proteins. Interestingly, Sav associates with the Warts (Wts, also called Lats) protein kinase, suggesting that Sav and Wts might function in a common signaling pathway (Tapon et al., 2002). Indeed, loss of wts also leads to increased cell proliferation and decreased apoptosis (Tapon et al., 2002). At present, little is known about the molecular architecture of this signaling pathway.

SUMMARY OF THE INVENTION

In accordance with the present invention, the inventors have identifed a new tumor suppressor gene now designated as hippo. The Hippo polypeptide induces suppression of tumor growth and tumor progression, apoptosis, and causes alteration of cell cycle kinetics. Thus, the present invention provides Hippo and Hippo genes, as well as methods of using Hippo and Hippo genes.

An embodiment of the present invention is an isolated polynucleotide encoding a polypeptide comprising an amino acid sequence of a Hippo polypeptide, e.g., SEQ ID NO:2 or 4. There is also provided a Hippo nucleic acid, e.g., SEQ ID NO:1 or 3. Further provided is an isolated polypeptide comprising the amino acid sequence of SEQ ID NO:2 or 4. Another embodiment is a nucleic acid of 15 to about 100 base pairs comprising from 15 contiguous base pairs of SEQ ID NO:1 or 3, or the complement thereof. A further embodiment includes from about 20, 25, 30, 40, 50 or 100 contiguous base pairs of SEQ ID NO:1 or 3, or the complement thereof.

Another embodiment of the invention is an isolated peptide having between 10 and about 50 consecutive residues of SEQ ID NO:2 or 4. Further, the peptide may comprise 15, 20, 25, or 30 consecutive residues of SEQ ID NO:2 or 4. In this application, "about" is defined as within +or −2 amino acids.

Yet another embodiment is an expression cassette comprising a polynucleotide encoding a polypeptide having the sequence of SEQ ID NO:2 or 4, wherein the polynucleotide is under the control of a promoter operable in eukaryotic cells. In another embodiment, the promoter of this expression cassette is heterologous to the coding sequence. The promoter may be a tissue specific and inducible promoter. In another embodiment, the expression cassette may be contained in a viral vector. The viral vector may be a retroviral vector, an adenoviral vector, and adeno-associated viral vector, a vaccinia viral vector, or a herpesviral vector. In a further embodiment the expression cassette may comprise a polyadenylation signal.

Another embodiment is a cell comprising an expression cassette comprising a polynucleotide encoding a polypeptide having the sequence of SEQ ID NO:2 or 4, wherein the polynucleotide is under the control of a promoter operable in eukaryotic cells, the promoter being heterologous to the polynucleotide.

Yet another embodiment of the invention is a monoclonal antibody that binds immunologically to a polypeptide comprising SEQ ID NO:2 or 4, or an immunologic fragment thereof. Also provided is a Hippo-binding monoclonal antibody with a detectable label. The label may be a fluorescent label, a chemiluminescent label, a radiolabel or an enzyme. Another embodiment of the invention is a hybridoma cell that produces a monoclonal antibody that binds immunologically to a polypeptide comprising SEQ ID NO:2 or 4, or an immunologic fragment thereof. A further embodiment is a polyclonal antisera, antibodies of which bind immunologically to a polypeptide comprising SEQ ID NO:2 or 4, or an immunologic fragment thereof.

Yet another embodiment is an isolated and purified nucleic acid that hybridizes, under high stringency conditions, to a DNA segment comprising SEQ ID NO:1 or 3, or the complement thereof. In a further embodiment, the nucleic acid is about 15, 17, 20 or 25 bases in length.

Another embodiment of the invention is a method of diagnosing cancer in a subject comprising the steps of (i) obtaining a biological sample from the subject, and (ii) assessing the expression of a functional Hippo or Mst2 product in sample. In a further embodiment, the sample is a tissue sample. The tissue sample may be brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow or blood tissue. In another embodiment, the assessing comprises detecting a nucleic acid encoding Hippo or Mst2. Detecting may comprise amplification the nucleic acid, nucleic acid hybridization, or sequencing. In another embodiment, assessing comprises detecting a Hippo or Mst2 polypeptide. The detecting of a Hippo or Mst2 polypeptide may comprise ELISA or immunohistochemistry. In yet another embodiment, the assessing may comprise wild-type or mutant oligonucleotide hybridization, with the oligonucleotide configured in an array on a chip or wafer. In another embodiment of the invention, the expression of Hippo or Mst2 is compared with the expression of Hippo or Mst2 in normal samples. In another embodiment, the comparison involves evaluating the level of Hippo or Mst2 expression or transcript stability/turnover.

Another embodiment is a non-human transgenic animal lacking one or both functional alleles of Hippo or Mst2. Also provided is a non-human transgenic animal that overexpresses Hippo or Mst2 as compared to a similar non-transgenic animal. In a further emodiment is a non-human transgenic animal, the genome of which comprises an expression cassette comprising a Hippo or Mst2 under the control of an inducible promoter.

An embodiment of the invention is a method for suppressing growth of a tumor cell comprising contacting the cell with an expression cassette comprising (a) a nucleic acid encoding Hippo or Mst2, and (b) a promoter active in the tumor cell, under conditions permitting the uptake of the nucleic acid by the tumor cell. In another embodiment, the tumor cell is derived from a brain tumor, lung tumor, liver tumor, spleen tumor, kidney tumor, lymph node tumor, small intestine tumor, blood cell tumor, pancreatic tumor, colon tumor, stomach tumor, cervix tumor, breast tumor, endometrial tumor, prostate tumor, testicle tumor, ovarian tumor, skin tumor, head and neck tumor, esophageal tumor, oral tissue tumor, or bone marrow tumor. In a further embodiment, the nucleic acid is contained in a viral vector. The viral vector may be a retroviral vector, an adenoviral vector, and adeno-associated viral vector, a vaccinia viral vector, and a herpesviral vector. In yet another embodiment, the nucleic acid is contained in a liposome.

Another embodiment of the invention is a method of altering the phenotype of a tumor cell comprising contacting the cell with an expression cassette comprising (a) a nucleic acid encoding Hippo or Mst2, and (b) a promoter active in the tumor cell, under conditions permitting the uptake of the nucleic acid by the tumor cell. In another embodiment, the phenotype is selected from the group consisting of cell proliferation, cell migration, contact inhibition, soft agar growth, cell cycling, invasiveness, tumorigenesis, and metastatic potential. The promoter may be a cytomegalovirus (CMV) promoter.

Another embodiment involves a method of inhibiting cancer in a subject suffering therefrom comprising administering to the subject an expression cassette comprising (a) a nucleic acid encoding Hippo or Mst2 polypeptide, and (b) a promoter active in tumor cells of the subject, whereby expression of the polypeptide inhibits the cancer. In a further embodiment, the subject is a human. In other embodiments, the nucleic acid encodes Hippo or Mst2. In another embodiment, the cancer is a selected from the group consisting of brain cancer, lung cancer, liver cancer, spleen cancer, kidney cancer, lymph node cancer, small intestine cancer, blood cell cancer, pancreatic cancer, colon cancer, stomach cancer, cervix cancer, breast cancer, endometrial cancer, prostate cancer, testicle cancer, ovarian cancer, skin cancer, head and neck cancer, esophageal cancer, oral tissue cancer, and bone marrow cancer. In yet another embodiment, the expression cassette is contained in a viral vector. The viral vector may be a retroviral vector, an adenoviral vector, and adeno-associated viral vector, a vaccinia viral vector, and a herpesviral vector. In another embodiment, the expression cassette is contained in a liposome. In another embodiment, the expression cassette further comprises a poly-A sequence. The poly-A sequence may be a bovine growth hormone (BGH) poly-A sequence. In a further embodiment, the expression cassette is administered intratumorally, in the tumor vasculature, local to the tumor, regional to the tumor, or systemically.

Also provided as part of a method of inhibiting cancer is the administration of a chemotherapuetic agent to the subject. The chemotherapeutic comprises cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate. The method of inhibiting cancer may also comprise administering radiation to the subject. In another embodiment, the radiation may be delivered local to a cancer site or is whole body radiation. The radiation may comprise γ-rays, X-rays, accelerated protons, microwave radiation, UV radiation or the directed delivery of radioisotopes to tumor cells. In yet another embodiment, a a second anticancer gene may be administered to the subject. The second anticancer gene may be a tumor suppressor. The second anticancer gene may be an inhibitor of apoptosis. In another embodiment, the second anticancer gene is an oncogene antisense construct.

An embodiment of the invention is a method of treating a subject with cancer, comprising the step of administering to the subject a Hippo or Mst2 polypeptide. The cancer may be selected from the group consisting of brain cancer, lung cancer, liver cancer, spleen cancer, kidney cancer, lymph node cancer, small intestine cancer, blood cell cancer, pancreatic cancer, colon cancer, stomach cancer, cervix cancer, breast cancer, endometrial cancer, prostate cancer, testicle cancer, ovarian cancer, skin cancer, head and neck cancer, esophageal cancer, oral tissue cancer, and bone marrow cancer. In a further embodiment, the polypeptide may be contained within a liposome. The liposome may be comprised of N-(1-[2,3-Dioleoyloxy]propyl)-N,N,N-trimethylammonium (DOTAP) and cholesterol. In another embodiment, the subject is a human.

Another embodiment of the invention comprises a method of screening a candidate substance for anti-tumor activity comprising the steps of (i) providing a cell lacking a functional Hippo or Mst2 polypeptide, (ii) contacting the cell with the candidate substance, and (iii) determining the effect of the candidate substance on the cell. In another embodiment, the cell is a tumor cell. In another embodiment, the determining may comprise comparing one or more characteristics of the cell in the presence of the candidate substance with the same one or more characteristics of a similar cell in the absence of the candidate substance. In a further embodiment, the characteristic is selected from the group consisting of Hippo or Mst2 expression, phosphatase activity, proliferation, metastasis, contact inhibition, soft agar growth, cell cycle regulation, tumor formation, tumor progression, metastasis and tissue invasion. In another embodiment, the candidate substance is a chemotherapeutic or radiotherapeutic agent. The candidate substance may also be selected from a small molecule library. In further embodiments, the cell is contacted in vitro or in vivo.

An additional embodiment of the invention is a method of screening a candidate substance for anti-tumor activity comprising the steps of (i) providing a cell, (ii) contacting the cell with the candidate substance, and (iii) determining the effect of the candidate substance on expression of a Hippo or Mst2 polypeptide.

Another embodiment is a method of producing a Hippo or Mst2 polypeptide in a host cell comprising (a) providing an expression cassette comprising a nucleic acid encoding Hippo or Mst2 operably linked to a promoter active in the host cell, (b) transferring the expression cassette into the host cell, and (c) culturing the host cell under conditions permitting expression of the Hippo or Mst2 polypeptide.

As used herein the specification, "a" or "an" may mean one or more. As used herein in the claim(s), when used in conjunction with the word "comprising", the words "a" or "an" may mean one or more than one. As used herein, "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIGS. 1A-B) Scanning electron micrographs (SEM) of a wild-type (A) and a fly head composed predominantly of hpo cells (FIG. 1B). The genotypes are (FIG. 1A) y w ey-flp; FRT42D/FRT42D w$^+$l(2)c1-R11 and (FIG. 1B) y w ey-flp; hpo$^{42-47}$ FRT42D/FRT42D w$^+$l(2)c1-R11. (FIG. 1C) Same as in FIG. 1B except that the side view of the compound eye is shown. Note presence of folded eye tissues and a general lack of ommatidia facets. (FIG. 1D) SEM of a compound eye composed predominantly of hpo$^{42-20}$ mutant cells. The eye is less folded and many ommatidial facets are discernable. The genotype is y w ey-flp; hpo$^{42-20}$ FRT42D/FRT42D w$^+$l(2)c1-R11. (FIG. 1E) SEM of a *Drosophila notum* containing a hpo clone. The mutant clone is outlined by the dashed line. (FIG. 1F) A high magnification view of epidermal cells near the border of a hpo clone on the notum. The dashed line marks the border between the wild-type cells and the mutant clone. The mutant clone is located to the right of the border. (FIG. 1G) A *Drosophila* wing containing a hpo clone as outlined by the dashed line. Note the blister-like phenotype in the mutant clone. (FIG. 1H) A portion of a *Drosophila* leg containing hpo mutant clones as outlined by the dashed lines. (FIG. 1I) Section through a hpo clone in the adult eye. The mutant clone is marked by the absence of pigment. Note the increase in spacing between mutant photoreceptor clusters. (FIGS. 1J-J") Third instar eye disc was stained with phalloidin (red), which highlights the outlines of the cells. hpo$^-$ cells were marked by the lack of GFP signal (green). Three images are shown, one of GFP (FIGS. 1J), one of phalloidin (FIG. 1J') and one of superimposed GFP and phalloidin (FIG. 1J"). Supernumerary interommatidial cells are present in hpo clones. (FIGS. 1K-K") and (FIGS. 1L -L"), similar to (FIGS. 1J-J") except that the disc was stained for the neuronal specific Elav protein (FIGS. 1K-K") or R8 specific Senseless (Sens) protein (FIGS. 1J-J"). Arrowhead marks the MF.

(FIGS. 2A-A") S-phase was labeled by BrdU incorporation (red). Two images are shown, one of GFP (FIG. 2A) and one of superimposed GFP and BrdU staining (FIG. 2A"). While normally detected in a single band of cells in SMW (arrowhead), BrdU incorporation continues posterior to SMW in hpo mutant clones. (FIGS. 2B-B") Similar to FIGS. 2A-A" except that pupal eye disc was analyzed at 16 hr APF. (FIGS. 2C-C") A 16 hr APF pupal eye stained for M-phase marker phospho-H3 (PH3). (FIG. 2D) Flow cytometric analysis of dissociated wing imaginal discs containing hpo mutant clones. The DNA profiles of hpo and wild-type cells are indicated by red and green traces, respectively. The insect shows forward scattering (FSC), which measures cell size. (FIGS. 2E-E") A third instar eye disc stained with α-CycE (red), which normally reveals a band of intense staining in the SMW (arrowhead) and diminished expression posterior to the SMW. Note the elevated CycE staining posterior to the SMW in hpo mutant clones (arrows). Elevated CycE level was also seen in hpo mutant cells immediately anterior to the SMW (yellow arrow). (FIGS. 2F-F") hpo mutant clones were generated in flies containing a cycE-lacZ reporter. The eye disc was stained for lacZ protein (red). Note the elevated level of cycE-lacZ in hpo clones. (FIGS. 2G-I) SEM images of compound eyes from wild-type (FIG. 2G), CYE$^{JP}$/cycE$^{AR95}$ (FIG. 2H) and cyE$^{JP}$ hpo$^{42-47}$/cycE$^{AR95}$+(FIG. 2I).

(FIGS. 3A-A") TUNEL staining (red) of a 36 hr APF pupal eye. Cell death is absent in hpo clones but abundant in the neighboring wild-type cells. (FIGS. 3B-B") Similar to FIGS. 3A-A" except that cell death was detected with α-active Drice. Arrows indicate two hpo clones. Note that cell death is largely confined to wild-type cells. (FIGS. 3C-C") A 36 hr pupal eye stained with α-DIAP1 antibody (red). (FIGS. 3D-D") Third instar eye disc stained with α-DIAP1 antibody (red). Arrowhead indicates MF. Note the elevated level of DIAP1 protein in hpo mutant cells irrespectively of their relative position to the MF. Yellow arrow indicates hpo mutant cells anterior to the MF. (FIGS. 3E-E") Third instar eye disc containing th$^{j5c8}$ and stained for lacZ protein (red). Arrowhead indicates MF. Note the elevated diap1-lacZ expression in hpo mutant cells irrespective of their relative position to the MF. Yellow arrow indicates hpo mutant cells anterior to the MF. (FIGS. 3F-F") Third instar eye disc containing the argos$^{W11}$ P[lacZ] enhancer trap and stained for lacZ (red). Note the similar level of argos-lacZ expression in hpo and wild-type cells.

(FIG. 4A) Genomic organization of the 56A-57B region. P-elements used in the mapping of hpo are shown as triangles. The genomic DNA fragment used in the rescue construct is indicated. The translation start and stop sites of hpo are also marked. (FIG. 4B) Sequence alignment of Hpo with MST2 and MST1. The 11 subdomains characteristic of protein kinases are indicated by Roman numerals. The C-terminal half of Hpo is less well conserved except for the last 60 amino acids. The K71R mutation that is used to generate kinase-dead Hpo is indicated. The boxed region represents the caspase cleavage site of MST1. Molecular lesions of hpo$^{42-20}$, hpo$^{42-47}$ and hpo$^{42-48}$ are indicated.

(FIGS. 5A-A") sav$^3$ clones were analyzed in third instar eye discs carrying th$^{j5c8}$. Note the elevated diap1-lacZ expression (red) in sav clones. Similar results were seen in sav$^4$ clones (not shown). (FIGS. 5B-B") Similar to (FIGS. 5A-A") except that wts$^{latsX1}$ mutant clones were analyzed. Note the elevated diap1-lacZ expression in wts clones. (FIG. 5C) RT-PCR analysis of total RNA extracted from control and hpo$^{42-47}$ 1$^{st}$ instar larvae. The diagram shows the major splicing form of the diap1 gene (Hay et al., 1995). th$^{j5c8}$ carries P[lacZ] insertion in the first (non-coding) exon (Hay et al., 1995). Also shown on the diagrams are diap1 primers (arrows) used in RT-PCR, with one set of primers spanning the intron (left gel) and the other set located within the second (coding) exon (right gel). Primers corresponding to rp49 gene are used as internal controls for RT-PCR. (FIG. 5D) Dosage sensitive genetic interactions between hpo, sav and wts. Heterozygous mutations of sav, wts, Tsc1 and Tsc2 were introduced into a hypomorphic hpo mutant background (see text for details). The percentage of flies surviving to adults is shown for various genotypes. The sav alleles used were sav$^3$ and sav$^4$. The wts alleles used were wts$^{latsX1}$ and Df(3R)tll-g. (FIGS. 5E-I) SEM images of compound eyes from the following genotype: GMR-hpo (FIG. 5E), GMR-P35; GMR-hpo (FIG. 5F); GMR-sav (FIG. 5G), GMR-wts (FIG. 5H) and GMR-hpo; GMR-sav (FIG. 5I).

(FIG. 6A) Unbiased yeast two-hybrid screens identify Hpo and Sav as interacting proteins. The schematic structures of Hpo and Sav proteins are shown at the top. "WW1+2" and "CC" refer to the two WW domains and the coiled-coil domain of Sav. Schematics of the bait and the interacting preys from each screen are shown. (FIG. 6B) Association between Hpo and Sav in vitro. S2 cell lysates were incubated with Glutathione Sepharose beads containing GST-Sav or GST-Tsc1 (as a control). Endogenous Hpo protein present in the cell lysates (lysate) or associated with the beads (pull-down) was probed with α-Hpo antibody. (FIG. 6C) Hpo, but not Wts, stimulates the phosphorylation of Sav in S2 cells. Lysates from S2 cells expressing various epitope-tagged proteins were probed with indicated antibodies. Expression of Hpo, but not Wts, results in mobility shift of the co-expressed Sav protein (lanes 1-3). (FIG. 6D) Phosphatase (CIP) treatment reversed the mobility shift of Sav induced by Hpo. (FIG. 6E) Hpo phosphorylates Sav in vitro. Myc-tagged Hpo or Hpo$^{K71R}$ was immunoprecipitated from S2 cells and tested for kinase activity against GST-Sav$^{362-607}$ and GST-Tsc1 (as a control substrate). The signal of GST-Sav phosphorylation by Hpo is indicated by an arrow. The arrowhead marks the expected migration position of the GST-Tsc1 and the asterisk indicates signals resulting from Hpo autophosphorylation. The input kinase and substrate are also shown (bottom two gels). (FIGS. 6F-I) Kinase-dead Hpo or C-terminal non-catalytic domain of Hpo behave in a dominant-negative manner. Drosophila wings from the following genotypes are shown: MS1096;+(FIG. 6F), MS1096; UAS-hpo (FIG. 6G), MS1096; UAS-hpo$^{K71R}$ (FIG. 6H) and MS1096; UAS-hpo$^{318-669}$ (FIG. 6I).

(FIG. 7A) Sav facilitates the phosphorylation of Wts by Hpo. Expression of Hpo, but not Sav, results in a mobility shift of the co-expressed Wts protein (compare lanes 2 and 3). Also note the supershift of Wts when both Sav and Hpo are expressed (compare lanes 3 and 4). Increasingly phosphorylated forms of Wts are indicated by small circles next to the protein bands, and filled with white, grey and black colors respectively. (FIG. 7B) Phosphatase (CIP) treatment reversed the mobility shift of Wts induced by Hpo. (FIG. 7C) Deletion mapping of the region of Wts phosphorylated by Hpo. The indicated Wts constructs were co-transfected into S2 cells with Hpo- and Sav-expressing plasmids. (FIG. 7D) Hpo phosphorylates Wts in vitro. Myc-tagged Hpo or Hpo$^{K71R}$ was immunoprecipitated from S2 cells and tested for kinase activity against GST-Wts$^{68-414}$ and GST-Tsc1. The signal of GST-Wts phosphorylation by Hpo is indicated by an arrow. The arrowhead marks the expected migration position of GST-Tsc1 and the asterisk indicates signals resulting from Hpo autophosphorylation. The input kinase and substrate are also shown (bottom two gels). (FIG. 7E) Hpo is required for Wts phosphorylation in vivo. Protein extracts from wild-type and hpo$^{42-47}$ 1$^{st}$ instar larvae were probed with antibodies against Wts and Hpo. Note the increased mobility of Wts from hpo$^-$ animals. Also note that Hpo appears as doublet in wild-type extracts due to autophosphorylation, but migrates as a single band in hpo$^{42-47}$, which produces a kinase-dead form of Hpo. (FIG. 7F) Association between Hpo and wild-type Sav or Sav$^{shrp6}$ was examined by co-immunoprecipitation wild-type Sav, but not Sav$^{shrp6}$, was detected in Myc-Hpo immunoprecipitates. (FIG. 7G) The coiled-coil domain of Sav is required for Sav to promote Wts phosphorylation by Hpo. Note that the supershift of Wts is observed when wild-type Sav (lane 3), but not Sav$^{shrp6}$ (lane 4), was expressed with Hpo. Increasingly phosphorylated forms of Wts are indicated by small circles next to the protein bands, and filled with white, grey and black colors respectively.

(FIGS. 8A-B) Dorsal view of Drosophila heads in which hpo function was selectively removed in the eye-antennal disc, in the absence (FIG. 8A) or presence (FIG. 8B) of the hsp70-MST2 transgene expression. The genotypes are (FIG. 8A) y w ey-flp; hpo$^{42-47}$ FRT42D/FRT42D w$^+$l(2)c1-R11 and (FIG. 8B) y w ey-flp; hpo$^{42-47}$ FRT42D/FRT42D w$^+$l(2)c1-R11; P[hsp70-MST2]. Both flies were treated by one 60 min heat-shock (at 38° C.) per day starting from the second instar larval stage until eclosion. Note the highly folded head cuticles and eye tissues in (FIG. 8A), which were completely suppressed by expression of MST2 (FIG. 8B). The boxed areas in (FIGS. 8A-B) are shown at higher magnification in (FIG. 8E-F). (FIG. 8C-D) Similar to (FIG. 8A-B) except that SEM images of compound eyes instead of the heads are shown. hsp70-MST2 was absent in (FIG. 8C), but present in (FIG. 8D). Note the highly disorganized eye structure in (FIG. 8C) and the near wild-type appearance of the compound eye in (FIG. 8D). (FIGS. 8E-F) High magnification view of the boxed areas in (A-B), showing detailed morphology of head cuticles. hsp70-

MST2 was absent in (FIG. 8E), but present in (FIG. 8F). Note the distinct cell-cell boundaries and the honeycomb-like appearance of the mutant epidermal cells (FIG. 8E), which was not seen in animals expressing MST2. (FIG. 8G) A tentative model of the Hpo-Sav-Wts pathway in size control. Hpo associates with and phosphorylates Sav. Hpo/Sav interaction promotes the phosphorylation of Wts by Hpo. Potential downstream effectors of the pathway are also illustrated.

SEQUENCE SUMMARY

Figure 1:
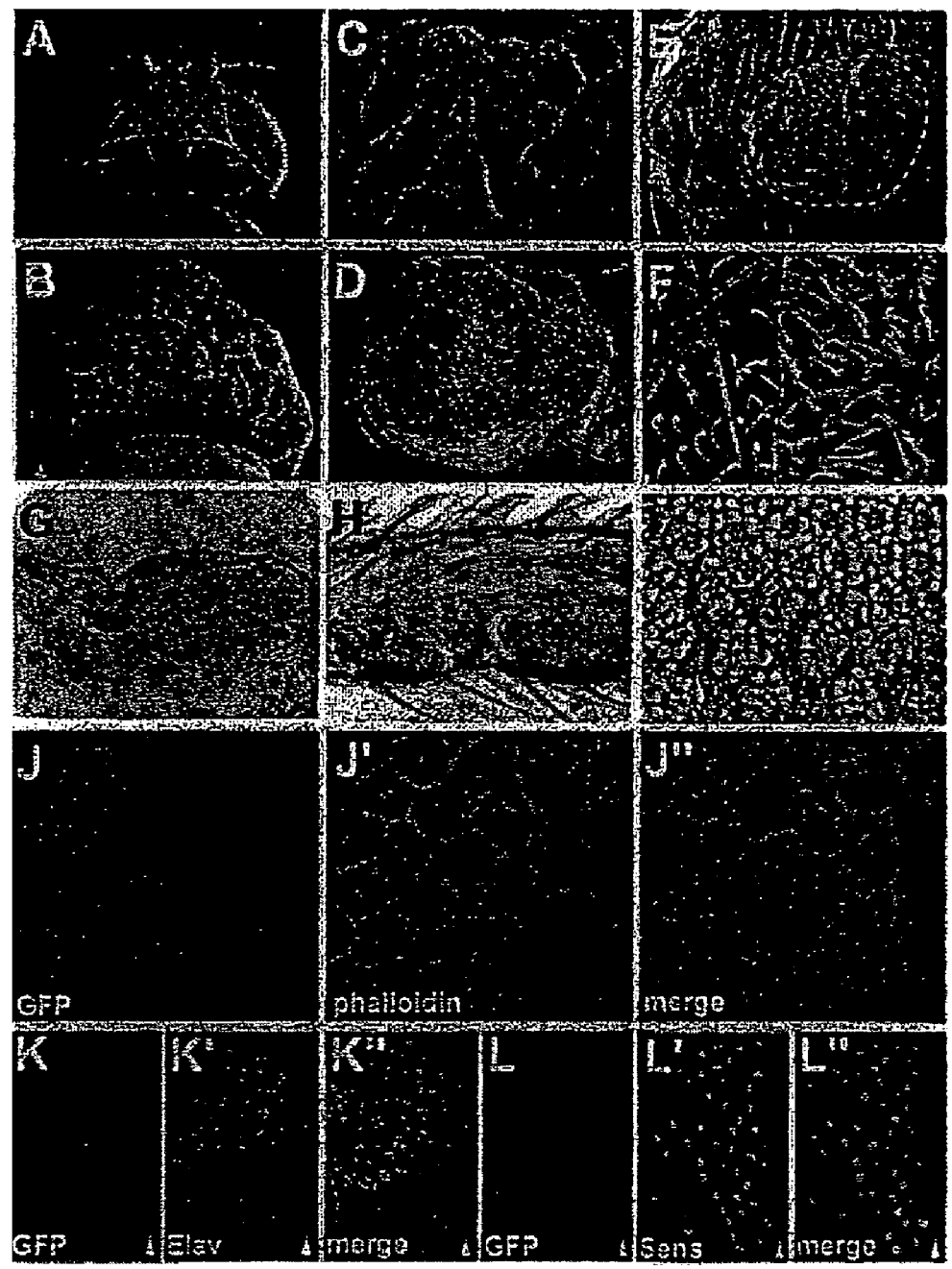
FIGS. 1A-L"—Loss of hpo Results in Tissue Overgrowth.

SEQ ID NO:1=Hippo nucleotide sequence (*Drosophila*)
SEQ ID NO:2=Hippo amino acid sequence (*Drosophila*)
SEQ ID NO:3=Mst2 nucleotide sequence (Human)
SEQ ID NO:4=Mst2 amino acid sequence (Human)

DETAILED DESCRIPTION OF THE INVENTION

Cancer is the result in the occurrence of multiple factors. Mutations may occur in proto-oncogenes that cause cellular proliferation to increase. Mutations also may occur in tumor suppressors whose normal function is to regulate cellular proliferation. Mutations in DNA repair enzymes impair the ability of the cell to repair damage before proliferating. Tumor suppressor genes are normal genes whose absence (loss or inactivation) can lead to cancer. Tumor suppressor genes encode proteins that slow cell growth and division. Cancer arises when there is a mutation in both alleles. Tumor suppressor genes (TSGs) play a major role in the pathogenesis of human lung cancer and other cancers. Known TSGs such as Rb and p53 have been found at chromosome regions 3p, 5q, 6p, 8p, 9p, and 11p as well as other sites, and have provided incredibly valuable in diagnosing and treating cancer. Since present inventor has now shown that Hippo and Mst2 satisfy the definitions of tumor suppressors, the corresponding genes and proteins may now be used for the early detection, diagnosis, and monitoring of prevention for various human cancers, as well as therapeutic efforts.

I. Function of Hippo and Mst2 as Tumor Suppressors

One of the criteria for defining the role of genes as tumor suppressor genes is to demonstrate that the tumor phenotype marked by inactivation of the genes can be rescued by the replacement of the wild-type alleles of these genes. If the frequent loss of heterozygosity (LOH), homozygous deletion, or, in some cases, abnormal transcripts and mutations of genes are the targets of carcinogens and the loss of function of genes leads to human cancers, then replacement of the abnormal genes with the wild-type genes would result in tumor suppression similar to that shown by the Rb or p53 tumor suppressor gene including inhibition of tumor cell growth in vitro, suppression of tumorigenicity and tumor growth, and inhibition of tumor cell invasion and metastasis in vivo.

Here, the inventor reports the identification of hippo (hpo) as a gene that regulates both cell proliferation and cell death in *Drosophila*. hpo encodes a Ste-20 family protein kinase that binds to and phosphorylates the tumor suppressor protein Salvador (Sav), which is known to interact with the Warts (Wts) protein kinase. Loss of hpo results in elevated transcription of the cell cycle regulator cyclin E and the cell-death inhibitor diap1, leading to increased proliferation and reduced apoptosis. The inventor has also shown that hpo, sav, and wts define a pathway that regulates diap1 at the transcriptional level. A human homolog of hpo, Mst2 (U.S. Pat. No. 6,500,938), completely rescues the overgrowth phenotype of *Drosophila* hpo- mutants, suggesting that hpo plays a conserved role in growth control in mammals.

II. Hippo Proteins

In addition to the entire Hippo protein, the present invention also relates to fragments of the polypeptides that may or may not retain the tumor suppressing activity. The entire length of Hippo is 669 amino acids. Fragments, including the N-terminus of the molecule may be generated by genetic engineering of translation stop sites within the coding region (discussed below). Alternatively, treatment of Hippo with proteolytic enzymes, known as proteases, can produce a variety of N-terminal, C-terminal and internal fragments. Examples of fragments may include contiguous residues of the Hippo sequence of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Purification of Protein

It may be desirable to purify Hippo or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; sodium dodecyl sulfate/polyacrylamide gel electrophoresis (SDS/PAGE); isoelectric focusing. A particularly efficient method of purifying peptides is fast protein liquid chromatography or HPLC.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate.

Separation can be accomplished in a matter of minutes, or at most an hour. Moreover, only a very small volume of the sample is needed because the particles are so small and close-packed that the void volume is a very small fraction of the bed volume. Also, the concentration of the sample can be low because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is little adsorption, less zone spreading and the elution volume is directly related to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. It should be possible to elute the substance without destroying the sample or the ligand. One of the most common forms of affinity chromatography is immunoaffinity chromatography. The generation of antibodies that would be suitable for use in accord with the present invention is discussed below.

The present invention also describes smaller Hippo-related peptides for use in various embodiments of the present invention. Because of their relatively small size, the peptides of the invention also can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

The present invention also provides for the use of Hippo proteins or peptides as antigens for the immunization of animals relating to the production of antibodies. A biospecific or multivalent composition or vaccine is produced. It is envisioned that the methods used in the preparation of these compositions will be familiar to those of skill in the art and should be suitable for administration to animals, i.e., pharmaceutically acceptable.

B. Variants

Variants of Hippo also are contemplated. Amino acid sequence variants of these polypeptides can be substitutional, insertional or deletion variants. Deletion variants lack one or more residues of the native protein that are not essential for function or immunogenic activity. Another common type of deletion variant is one lacking secretory signal sequences or signal sequences directing a protein to bind to a particular part of a cell. Insertional mutants typically involve the addition of material at a non-terminal point in the polypeptide, such as the insertion of an immunoreactive epitope or even a single residue. Terminal additions are called fusion proteins.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventor that various changes may be made in the DNA sequences of genes without appreciable loss of their biological utility or activity, as discussed below. Table 1 shows the codons that encode particular amino acids.

Amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine, and isoleucine.

III. Nucleic Acids

In addition, it should be clear that the present invention is not limited to the specific nucleic acids disclosed herein. As discussed below, "Hippo" and "Mst2" may contain a variety of different bases and yet still produce a corresponding polypeptide that is functionally indistinguishable, and in some cases structurally, genes disclosed herein.

Nucleic acids according to the present invention may encode an entire Hippo or Mst2 gene, a domain of Hippo or Mst2, or any other fragment of the Hippo or Mst2 sequences set forth herein. The nucleic acid may be derived from genomic DNA, i.e., cloned directly from the genome of a particular organism. In other embodiments, however, the nucleic acid would comprise complementary DNA (cDNA).

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given Hippo or Mst2 from a given species may be represented by natural variants that have slightly different nucleic acid sequences but, nonetheless, encode the same protein (Table 1). As used in this application, the term "polynucleotide having the nucleic acid sequence of SEQ ID NO:1 or 3" refers to a nucleic acid molecule that has been isolated free of total cellular nucleic acid. A functionally equivalent codon is a codon that encodes the same amino acid, such as the six codons for arginine or serine (Table 1), and also refers to codons that encode biologically equivalent amino acids.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The DNA segments of the present invention include those encoding biologically functional equivalent Hippo proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

A. Hybridization

Naturally, the present invention also encompasses DNA segments that are complementary, or essentially complementary, to the sequences encoding Hippo or Mst2. Nucleic acid sequences that are "complementary" are those that are capable of base-pairing according to the standard Watson-Crick complementary rules. As used herein, the term "complementary" means nucleic acid sequences that are substantially complementary, as may be assessed by the same nucleotide comparison set forth above, or as defined as being capable of hybridizing to the aforementioned nucleic acid segment under relatively stringent conditions such as those described herein. Such sequences may encode the entire Hippo or Mst2 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, or 1000 bases and longer are contemplated as well. Such oligonucleotides will find use, for example, as probes in Southern and Northern blots, in situ tissue hybridization and as primers in amplification reactions.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM MgCl2, 10 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C. Formamide and SDS also may be used to alter the hybridization conditions.

B. Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In other embodiments, the probes or primers are labeled with radioactive species ($^{32}$P, $^{14}$C, $^{35}$S, $^{3}$H, or other label), with a fluorophore (rhodamine, fluorescein) or a chemilluminescent (luciferase).

One method of using probes and primers of the present invention is in the search for genes related to Hippo or, more particularly, orthologs of Hippo from other species, such as Mst2 from humans. Normally, the target DNA will be a genomic or cDNA library, although screening may involve analysis of RNA molecules. By varying the stringency of hybridization, and the region of the probe, different degrees of homology may be discovered.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In other embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, it is envisioned that the probes or primers described herein will be useful as reagents in solution hybridization, as in PCR™, for detection of expression of corresponding genes, as well as in embodiments employing a solid phase. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

C. Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety. Other methods of amplication are ligase chain reaction (LCR), Qbeta Replicase, isothermal amplification, strand displacement amplification (SDA), PCR™-like template- and enzyme-dependent synthesis using primers with a capture or detector moiety, transcription-based amplification systems (TAS), cylical synthesis of single-stranded and double-stranded DNA, "RACE", one-sided PCR™, and di-oligonucleotide amplification.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

IV. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al. (1988) and Ausubel et al. (1994), both incorporated herein by reference.

The term "expression cassette" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Such promoters may be used to drive β-galactosidase expression for use as a reporter gene. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al., (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |

TABLE 2-continued

Promoter and/or Enhancer

| Promoter/Enhancer | References |
| --- | --- |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al,. 1999), the somatostatin receptor 2 gene (Kraus et al., 1998), murine epididymal retinoic acid-binding gene (Lareyre et al., 1999), human CD4 (Zhao -Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

B. Regulatory Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

In expression, one will typically include a polyadenylation signal to effect proper polyadenylation of the transcript. The nature of the polyadenylation signal is not believed to be crucial to the successful practice of the invention, and/or any such sequence may be employed. Specific embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

C. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Examples of selectable and screenable markers are well known to one of skill in the art.

D. Host Cells

In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

E. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia

*methanolica*. One of skill in the art would know how to express a vector, such as an expression construct, to produce a nucleic acid sequence or its cognate polypeptide, protein, or peptide.

F. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the methods for in vivo delivery involves the use of an adenovirus expression vector. "Adenovirus expression vector" is meant to include those constructs containing adenovirus sequences sufficient to (a) support packaging of the construct and (b) express an antisense polynucleotide that has been cloned therein. In this context, expression does not require that the gene product be synthesized.

1. Adenovirus Expression Vectors

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retrovirus Expression Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

3. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

4. Non-Viral Methods for Gene Transfer

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

In still another embodiment, the transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor -mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes - as non-anchorage dependent cells growing in suspension throughout the bulk of the culture or as anchorage-dependent cells requiring attachment to a solid substrate for their propagation (i.e., a monolayer type of cell growth).

V. Antibodies

The antibodies to Hippo and Mst2 are useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further below.

In another aspect, the present invention contemplates an antibody that is immunoreactive with a Hippo molecule of the present invention, or any portion thereof. An antibody can be a polyclonal or a monoclonal antibody. In one embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to Hippo-related antigen epitopes. Additionally, it is proposed that monoclonal antibodies specific to the particular Hippo of different species may be utilized in other useful applications In general, both polyclonal and monoclonal antibodies against Hippo or Mst2 may be used in a variety of embodiments. For example, they may be employed in antibody cloning protocols to obtain cDNAs or genes encoding other Hippo or Mst2. They may also be used in inhibition studies to analyze the effects of Hippo- or Mst2-related peptides in cells or animals. Anti-Hippo or -Mst2 antibodies also will be useful in immunolocalization studies to analyze the distribution of Hippo during various cellular events, for example, to determine the cellular or tissue-specific distribution of Hippo or Mst2 polypeptides under different points in the cell cycle. A particularly useful application of such antibodies is in purifying native or recombinant Hippo or Mst2, for example, using an antibody affinity column. The operation of all such immunological techniques will be known to those of skill in the art in light of the present disclosure. Means for preparing and characterizing antibodies are well known in the art (see, e.g., Harlow and Lane, 1988; U.S. Pat. 4,196,265).

VI. Diagnosing Cancers Involving Hippo or Mst2

Hippo, Mst2 and the corresponding genes may be employed as a diagnostic or prognostic indicator of cancer. More specifically, point mutations, deletions, insertions or regulatory perturbations relating to Hippo or Mst2 may cause cancer or promote cancer development, cause or promoter tumor progression at a primary site, and/or cause or promote metastasis. Other phenomena associated with malignancy that may be affected by Hippo or Mst2 expression include angiogenesis and tissue invasion.

A. Genetic Diagnosis

One embodiment of the instant invention comprises a method for detecting variation in the expression of Hippo or Mst2. This may comprise determining that level of Hippo or Mst2 or determining specific alterations in the expressed product. Obviously, this sort of assay has importance in the diagnosis of related cancers. Such cancer may involve cancers of the brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow and blood tissue.

The biological sample can be any tissue or fluid. Various embodiments include cells of the brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow and blood tissue. Other embodiments include fluid samples such as peripheral blood, lymph fluid, ascites, serous fluid, pleural effusion, sputum, cerebrospinal fluid, lacrimal fluid, stool, or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have Hippo-related pathologies. In this way, it is possible to correlate the amount or kind of Hippo detected with various clinical states.

Alterations of a gene include deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of Hippo produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

1. Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

2. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

3. Kit Components

All the essential materials and reagents required for detecting and sequencing Hippo, Mst2 and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

4.- RT-PCR™ (Relative Quantitative)

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundancies made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

Still other studies may be performed using "real-time" RT-PCR™ (Higuchi et al., 1993). These assays detect PCR™ products as they accumulate instead of detecting the amount of PCR™ products accumulated after a fixed number of cycles. A method of detecting fluorescence after each PCR™ cycle is required. The fluorescence signal is plotted versus the cycle number. The cycle number is expressed as the threshold cycle ($C_T$). The initial fluorescence defines the baseline for the plot and an accumulated PCR™ product is indicated by an increase in fluorescence above the baseline. Quantification of the amount of target in a sample is determined by measuring and comparing the $C_T$ to a standard curve to determine the starting copy number.

"Real-Time" RT-PCR™ (Higuchi et al., 1993) provides more precise quantitation of the amount of target because it is determined during the exponential phase of PCR™, rather than at the endpoint. It also allows higher throughput because the use of $C_T$ values allow a larger dynamic range. Dilutions of each sample are no longer required.

B. Immunodiagnosis

Antibodies (discussed above) of the present invention can be used in characterizing the Hippo or Mst2 content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-Hippo or -Mst2 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation. Following formation of specific immunocomplexes between the test sample and the bound antibody, and subsequent washing, the occurrence and even amount of immunocomplex formation may be determined by subjecting same to a second antibody having specificity for Hippo that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease, alkaline phosphatase, glucose oxidase, or (horseradish) peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl -benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

C. Combination of Tumor Suppressors with Other Markers

Tumors are notoriously heterogeneous, particularly in advanced stages of tumor progression (Morton et al., 1993; Fidler and Hart, 1982; Nowell, 1982; Elder et al., 1989; Bystryn et al., 1985). Although tumor cells within a primary tumor or metastasis all may express the same marker gene, the level of specific mRNA expression can vary considerably (Elder et al., 1989). It is, in certain instances, necessary to employ a detection system that can cope with an array of heterogeneous markers.

Thus, while the present invention exemplifies various tumor suppressors as a markers, any marker that is correlated with the presence or absence of cancer may be used in combination with these markers to improve the efficacy of tumor detection and treatment. A marker, as used herein, is any proteinaceous molecule (or corresponding gene) whose production or lack of production is characteristic of a cancer cell. Depending on the particular set of markers employed in a given analysis, the statistical analysis will vary. For example, where a particular combination of markers is highly specific for melanomas or breast cancer, the statistical significance of a positive result will be high. It may be, however, that such specificity is achieved at the cost of sensitivity, i.e., a negative result may occur even in the presence of melanoma or breast cancer. By the same token, a different combination may be very sensitive, i.e., few false negatives, but has a lower specificity.

VII. Transgenic Animals/Knockout Animals

In one embodiment of the invention, transgenic flies or animals are produced which contain a functional transgene encoding a functional Hippo or Mst2 polypeptide or variants thereof. Transgenic flies or animals expressing Hippo or Mst2 transgenes, recombinant cell lines derived from such animals and transgenic embryos may be useful in methods for screening for and identifying agents that induce or repress function of Hippo or Mst2. Transgenic animals of the present invention also can be used as models for studying indications such as cancers.

In one embodiment of the invention, a Hippo or Mst2 transgene is introduced into a non -human host to produce a transgenic animal expressing a human or murine Hippo or Mst2 gene. The transgenic animal is produced by the integration of the transgene into the genome in a manner that permits the expression of the transgene. Methods for producing transgenic animals are generally described by Wagner and Hoppe (U.S. Pat. No. 4,873,191), Brinster et al. (1985), and "Manipulating the Mouse Embryo; A Laboratory Manual" 2nd edition (eds., Hogan, Beddington, Costantimi and Long, Cold Spring Harbor Laboratory Press, 1994), each of which are incorporated herein by reference in its entirety.

It may be desirable to replace the endogenous Hippo or Mst2 by homologous recombination between the transgene and the endogenous gene; or the endogenous gene may be eliminated by deletion as in the preparation of "knock-out" animals. Typically, a Hippo or Mst2 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particular embodiment, transgenic mice are generated which overexpress Hippo or Mst2 or express a mutant form of the polypeptide. Alternatively, the absence of a Hippo or Mst2 in "knock-out" mice permits the study of the effects that loss of Hippo or Mst2 protein has on a cell in vivo. Knock-out mice also provide a model for the development of Hippo- or Mst2-related cancers.

As noted above, transgenic animals and cell lines derived from such animals may find use in certain testing experiments. In this regard, transgenic animals and cell lines capable of expressing wild-type or mutant Hippo or Mst2 may be exposed to test substances. These test substances can be screened for the ability to enhance wild-type Hippo or Mst2 expression and or function or impair the expression or function of mutant Hippo or Mst2.

Promoter sequences mentioned within this document may be used to drive β-galactosidase expression. The use of a β-galactosidase reporter construct in transgenic mice may be used to identify factors which regulate Hippo or Mst2 expression.

VIII. Methods for Treating Cancers Using Hippo or Mst2

The present invention also involves, in another embodiment, the treatment of cancer. The types of cancer that may be treated, according to the present invention, is limited only by the involvement of Hippo or Mst2. By involvement, it is not even a requirement that Hippo or Mst2 be mutated or abnormal—the overexpression of Hippo or Mst2 may actually overcome other lesions within the cell. Thus, it is contemplated that a wide variety of cancer cells may be treated using Hippo or Mst2 therapy, including brain, lung, liver, spleen, kidney, lymph node, small intestine, blood cells, pancreas, colon, stomach, cervix, breast, endometrium, prostate, testicle, ovary, skin, head and neck, esophagus, oral tissue, bone marrow and blood tissue.

In many contexts, it is not necessary that the cancer cell be killed or induced to undergo normal cell death or "apoptosis." Rather, to accomplish a meaningful treatment, all that is required is that the tumor growth be slowed to some degree. It may be that the tumor growth is partially or completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventor is the intervention, at the molecular level, in the events involved in the tumorigenesis of some cancers. Specifically, one provides, to a cancer cell, an expression cassette capable of providing Hippo or Mst2 to that cell. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

B. Protein Therapy

Another therapy approach is the provision, to a subject, of Hippo or Mst2 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

C. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that Hippo replacement therapy could be used similarly in conjunction with chemo- or radiotherapeutic intervention. It also may prove effective to combine Hippo or Mst2 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a Hippo or Mst2 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either Hippo or Mst2 or the other agent will be desired. Various combinations may be employed, where Hippo or Mst2 is "A" and the other agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, accelerated protons, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a Hippo expression construct is particularly preferred as this compound.

In treating cancer according to the invention, one would contact the tumor cells with an agent in addition to the expression construct. This may be achieved by irradiating the localized tumor site with radiation such as X-rays, accelerated protons, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a Hippo expression construct, as described above.

Agents that directly cross-link nucleic acids, specifically DNA, are envisaged to facilitate DNA damage leading to a synergistic, antineoplastic combination with Hippo. Agents such as cisplatin, and other DNA alkylating agents may be used. Cisplatin has been widely used to treat cancer, with efficacious doses used in clinical applications of $20\, mg/m^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from $25$-$75\, mg/m^2$ at 21 day intervals for adriamycin, to $35$-$50\, mg/m^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, accelerated protons, and/or the directed delivery of radioisotopes to tumor cells. Other forms of DNA damaging factors are also contemplated such as microwaves, and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics Standards.

The inventor proposes that the regional delivery of Hippo or Mst2 expression constructs to patients with Hippo- or Mst2-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining Hippo- or Mst2-targeted therapies with chemo- and radiotherapies, it also is contemplated that combination with other gene therapies will be advantageous. For example, targeting of Hippo and p53 or p16 mutations at the same time may produce an improved anti-cancer treatment. Any other tumor-related gene conceivably can be targeted in this manner, for example, p21, Rb, APC, PTEN, mda-7, DCC, NF-1, NF -2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove useful by themselves in treating a Hippo- or Mst2-related disorder. In this regard, reference to chemotherapeutics and non-Hippo or Mst2 gene therapy in combination should also be read as a contemplation that these approaches may be employed separately.

D. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions. Upon formulation, solutions will be administered in a manner compatible with the dosage formulation and in such amount as is therapeutically effective.

IX. EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials and Methods

Drosophila Genetics. All crosses and staging were done at 25° C. Null alleles of sav and wts, including $sav^3$, $sav^4$ and $wts^{latsX1}$, as well as GMR-wts and GMR-sav lines were kindly provided by Iswar Hariharan. $th^{j5c8}$ and cycE-lacZ were gifts of Hermann Steller and Wei Du, respectively. $cycE^{JP}$ and $cycE^{AR95}$ were gifts from Helena Richardson and Christian Lehner, respectively. $Tsc1^{29}$ and $Tsc2^{192}$ alleles were described previously (Gao and Pan, 2001).

Molecular biology and yeast two hyrid screens. Genomic DNA was isolated from hpo mutant embryos and amplified with PCR. The PCR products were directly sequenced using primers spanning the hpo locus. A 4.0 kb genomic fragment containing just the hpo transcription unit was cloned into Casperhs-1, a modified Casperhs vector (Pan and Rubin, 1997), for the rescue experiment. A full-length hpo cDNA clone, GH10354, was obtained from Research Genetics, and used to generate UAS and GMR constructs. The MST2 cDNA was obtained from Research Genetics and cloned into the pCasper-hs vector to generate hsp70-MST2.

Myc-tagged Hpo, Flag-tagged Sav and V5/His-tagged Wts constructs were made using the pAc5.1/V5-HisB vector (Invitrogen). Sequences encoding the N-terminal Myc epitope (MEQKLISEEDLNE) or Flag epitope (MDYKDDDDK) was added by PCR in place of the first Met codon of the respective cDNA clones.

Yeast two-hybrid screens were carried out using Stratagene's CytoTrap system and Drosophila cDNA library according to manufacturer's instructions.

Cell transfection, immunoprecipitation, GST pulldown and in vitro kinase assays. Transfection and immunoprecipitation in S2 cells were carried out as described previously (Gao and Pan, 2001). GST pulldown assay was carried out as described (Tapon et al., 2002). For in vitro kinase assay, S2 cells expressing myc-tagged Hpo or $Hpo^{K71R}$ were lysed in lysis buffer containing 50 mM HEPES (pH7.4), 50 mM NaCl, 1 mM EDTA, 0.5% NP-40 plus phosphatase and protease inhibitors cocktail. Hpo was immunoprecipitated with anti-myc antibody and protein G-Sepharose. Immunoprecipitates were washed and incubated with recombinant substrate GST fusion proteins in kinase buffer containing 40 mM HEPES (pH7.4), 10 mM MgCl2, 10 μM ATP and 10 μCi/ml γ-$P^{32}$ATP at 30° C. for 45 minutes.

Histology and cell cycle analysis. Antibodies against Sens, CycE were gifts from Hugo Bellen and Terry Orr-Weaver respectively. Antibodies against Drice and DIAP1 were gifts from Bruce Hay.

FACS analysis of dissociated imaginal wing disc cells was performed as described (Neufeld et al., 1998) using FACStar machine and analyzed with CellQuest program. Cell doubling time analysis was carried out as described (Neufeld et al., 1998) using $hpo^{42-47}$ mutant clones induced at 48 hr AED and analyzed at 120 hr AED. Cell doubling times were derived using the formula (log 2/log N)hr, where N=median number of cells/clone and hr=time between heatshock and disc fixation.

Example 2

Results

Isolation of hpo mutants. The inventor used X-ray mutagenesis and FRT/FLP system to screen the *Drosophila* genome for genes that negatively regulate tissue growth. Three lethal mutations, 42-20, 42-47 and 42-48, define a single complementation, which was named hippo (hpo) based on the overgrowth phenotype in mosaic flies. All analyses in this report were performed using the null allele hpo$^{42-47}$ (see below) unless otherwise indicated. Selective removal of hpo function in over 90% of the eye disc cells using the eyeless-FLP technique (Newsome et al., 2000) resulted in flies with enlarged, folded eyes and excess head cuticle (FIGS. 1A -1C). The external ommatidial facets were frequently lost (FIG. 1C). hpo mutant clones induced in other tissues also resulted in overgrowth (FIGS. 1E-1H). In addition, the cuticle secreted by hpo mutant epidermal cells displays an unusual texture. In hpo mutant clones on the notum, the apical surface of the epidermal cells are clearly demarcated such that cell-cell boundaries are visible between adjacent cells, while cell boundaries are not visible in surrounding wild-type tissues (FIG. 1F). A similar phenotype is seen in hpo mutant clones on the leg (FIG. 1H) and the head cuticle (see FIG. 8E). This phenotype most likely reflects abnormal morphology of the epidermal cells as shown previously for wts mutant cells (Justice et al., 1995).

Among the three hpo alleles, hpo$^{42-47}$ elicited the most severe overgrowth, followed by hpo$^{42-48}$, with hpo$^{42-20}$ being the weakest allele. For example, eyes composed predominantly of hpo$^{42-20}$ cells have fewer folded eye tissues (FIG. 1D), when compared to similar eyes composed of hpo$^{42-47}$ cells (FIG. 1C). The external ommatidial facets are also more evident in eyeless-FLP-hpo$^{42-20}$ eyes (compare FIGS. 1D and 1C). The overgrowth phenotypes elicited by hpo$^{42-47}$ are qualitatively similar to those previously described for mutations of the *Drosophila* tumor suppressor genes sav and wts (Xu et al., 1995; Justice et al., 1995; Tapon et al., 2002; Kango-Singh et al., 2002). Overall, the hpo$^{42-47}$ phenotypes are more severe than those of null sav alleles but less severe than those of null wts alleles. This is also reflected by the different degrees of pupal lethality caused by removing hpo, sav or wts function in the eye using the eyeless-FLP technique. While over 90% of eyeless-FLP-hpo$^{42-20}$ animals survive to adults, only 30% of eyeless-FLP-hpo$^{42-48}$ animals and 2% of eyeless-FLP-hpo$^{42-47}$ animals survive to adults. For comparison, nearly all eyeless-FLP-sav$^3$ animals survive to adults, and none of eyeless -FLP-wts$^{latsX1}$ animals survive to adults.

hpo regulates cell proliferation. Sectioning of hpo mutant clones in adult eyes revealed a normal complement of photoreceptor cells (FIG. 1I), suggesting that photoreceptor differentiation is not perturbed by loss of hpo. However, spacing between photoreceptor clusters is increased due to the presence of extra interommatidial cells (FIG. 1I). These extra cells are pigment cells since they produced normal pigment when clones were induced in a w$^+$ background (data not shown). The formation of extra interommatidial cells is evident in late -third instar eye discs, when hpo mutant clones at the posterior region of the eye imaginal disc contain many additional cells between photoreceptor clusters (FIGS. 1J-J"). To investigate whether the extra cells are due to abnormal ommatidial spacing and/or cell differentiation during early retinal patterning, the inventor stained the eye imaginal discs for the neuronal marker Elav and the R8 marker Senseless (Sens). As seen in FIGS. 1K-1K" and 1L-1L", hpo mutant ommatidial clusters have the normal complement of differentiating photoreceptor cells (FIGS. 1K-1K"), and R8, the first photoreceptor cell to differentiate, is specified at correct location and density emerging from MF (FIGS. 1L-1L"). The spacing between adjacent ommatidial clusters is initially normal but increases at later stages, towards the posterior of the eye disc, due to the presence of extra interommatidial cells (FIGS. 1K-1K" and 1L-1L"). Thus, in hpo mutant clones, early retina patterning is not affected, and photoreceptors exit cell cycle and differentiate normally. However, hpo mutant clones contain an increased number of uncommitted, interommatidal cells in third instar eye discs.

Figure 2:
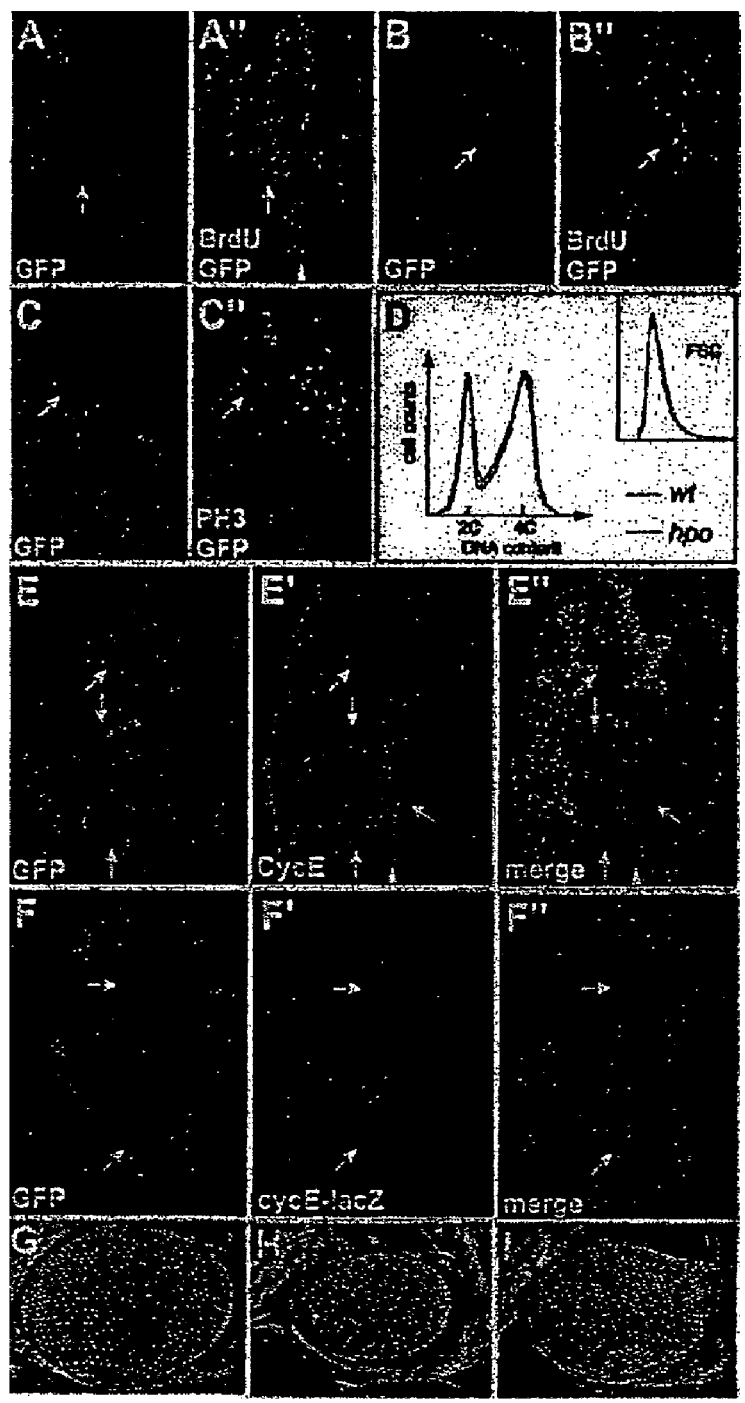
FIGS. 2A-I"—Cell cycle defects of hpo mutant cells. In all panels, hpo clones were marked by the absence of GFP signal (green) and indicated with arrows.

The increased number of interommatidial cells in hpo mutant clones could be due to increased cell proliferation, decreased apoptosis or a combination of both. To pinpoint the developmental cause of this phenotype, the inventor first monitored cell proliferation in the eye imaginal discs. The inventor used BrdU incorporation to label cells in the S phase. In wild-type eye discs, S-phase cells are distributed randomly anterior to the MF. Cells are arrested synchronously in G1 within the MF and do not incorporate BrdU. Posterior to the MF, cells in the SMW (arrowhead in FIGS. 2A and 2A") undergo a synchronous S phase that can be revealed as a band of cells BrdU positive cells. Few BrdU-positive cells are found posterior to the SMW. In hpo mutant clones, uncommitted interommatidial cells fail to undergo cell cycle arrest posterior to the SMW, and continue S-phase (FIGS. 2A and 2A"). At least some of these cells continue to proliferate during early pupal development, as revealed by ectopic BrdU incorporation (FIGS. 2B and 2B") and the M phase marker phosphorylated histone H3 (PH3) (FIGS. 2C and 2C") at 16 hr APF. hpo mutant cells in the compound eye eventually exit cell cycle and differentiate as pigment cells, and ectopic cell proliferation is undetectable beyond 24 hr APF (not shown).

To test whether hpo also affects the rate of cell multiplication during the growth phase of imaginal discs, the inventor measured cell-doubling time for hpo mutant cells in the wing imaginal disc. The cell-doubling time for wild-type clones and hpo mutant clones (142 pairs of clones analyzed) was 13.9 hrs and 12.2 hrs, respectively. Thus, hpo mutant cells multiply faster in the wing discs. FACS analysis of dissociated wing disc cells showed that hpo mutant cells have a similar cell cycle profile and cell size (FSC) distribution as compared to wild-type cells (FIG. 2D). Thus, loss of hpo does not accelerate a particular phase of the cell cycle during the growth period of imaginal discs. Rather, each phase of the cell cycle is proportionally accelerated.

Figure 3:
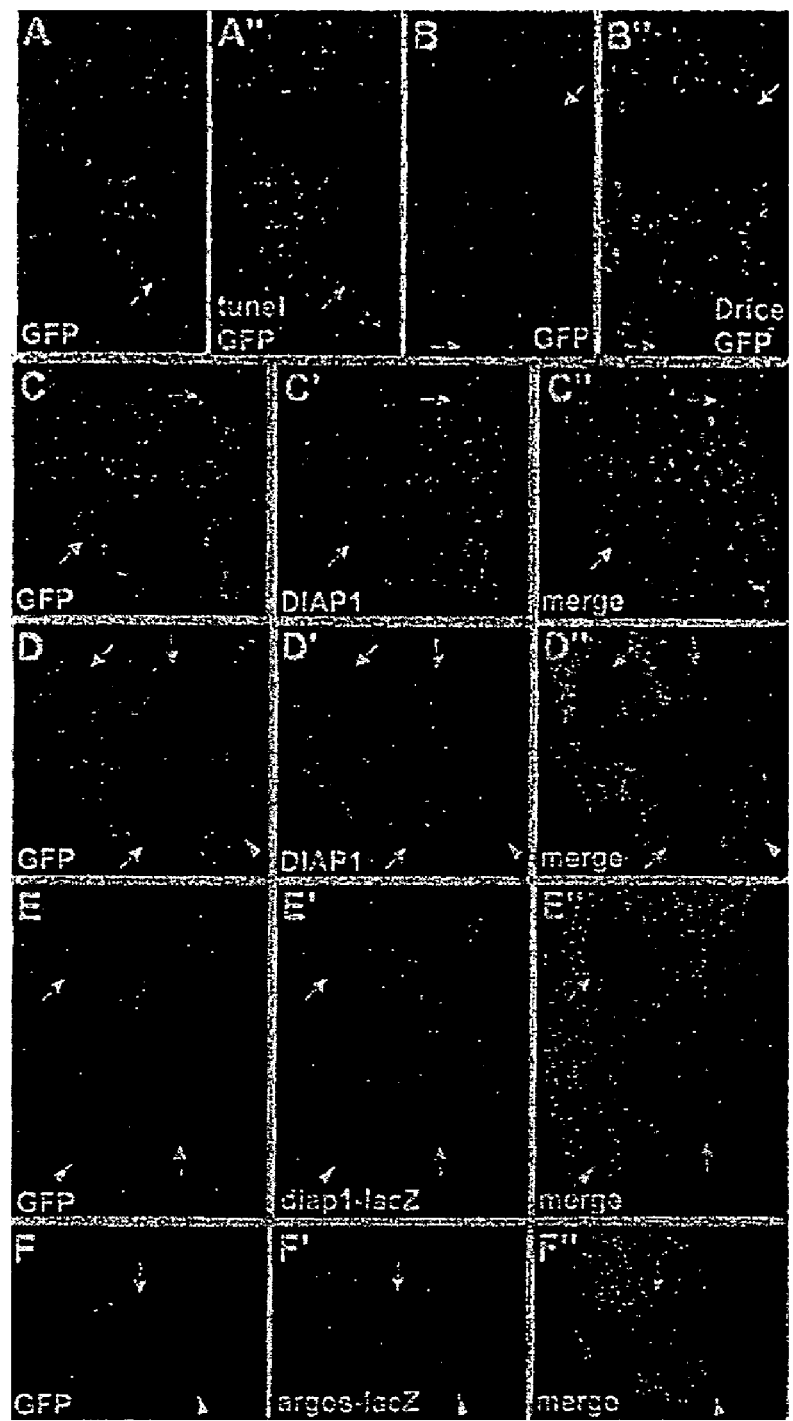
FIGS. 3A-F"—Cell death defects of hpo mutant cells.

A limiting factor for S-phase entry in *Drosophila* imaginal discs is Cyclin E (CycE) (Richardson et al., 1995; Neufeld et al., 1998). Thus, the inventor examined CycE level in hpo mutant clones in the eye imaginal discs. Elevated CycE protein was detected in hpo mutant cells in the SMW and posterior to it (FIGS. 2E-E"). Elevated CycE was also observed in hpo mutant cells just anterior to the SMW, although the effect was less profound (yellow arrow in FIGS. 2E -E"). To investigate whether the regulation of CycE level by hpo is mediated by transcriptional or post-transcriptional mechanisms, the inventor took advantage of a cycE-lacZ reporter that contains 16.4 kb of 5' regulatory sequence of cycE (Duman-Scheel et al., 2002). Expression of the cycE-lacZ reporter was increased in hpo mutant clones, suggesting that the elevated level of CycE protein is mediated, at least in part, by an increase in cycE transcription. The inventor further examined genetic interactions between cycE and hpo. cycE$^{JP}$/cycE$^{AR95}$ is an allelic combination that produces small and rough eye phenotype (FIG.2H). Both the roughness and eye size phenotype of this hypomorphic combination is dominantly suppressed by heterozygosity for hpo (FIG. 2I). Thus, cycE is a critical downstream target of hpo.

hpo regulates apoptosis. Developmental apoptosis is most prominent in pupal retina around 36 hr APF when a wave apoptosis removes excessive interommatidial cells (Wolff and Ready, 1993). The inventor assayed cell death using TUNEL or antibody against the activated caspase Drice (Yoo et al., 2002). Strikingly, in pupal eyes at 36 hr APF, cell death was suppressed in hpo mutant clones, even though abundant apoptosis was detected in the neighboring wild-type cells (FIGS. 3A-3A" and 3B-3B"). Cell death in hpo mutant clones is not simply delayed, since the inventor could not detect any significant cell death in hpo mutant clones up to 48 hr APF when the mature lattice of the retina is formed (data not shown). Thus, normal developmental apoptosis appears to require hpo function.

Figure 4:
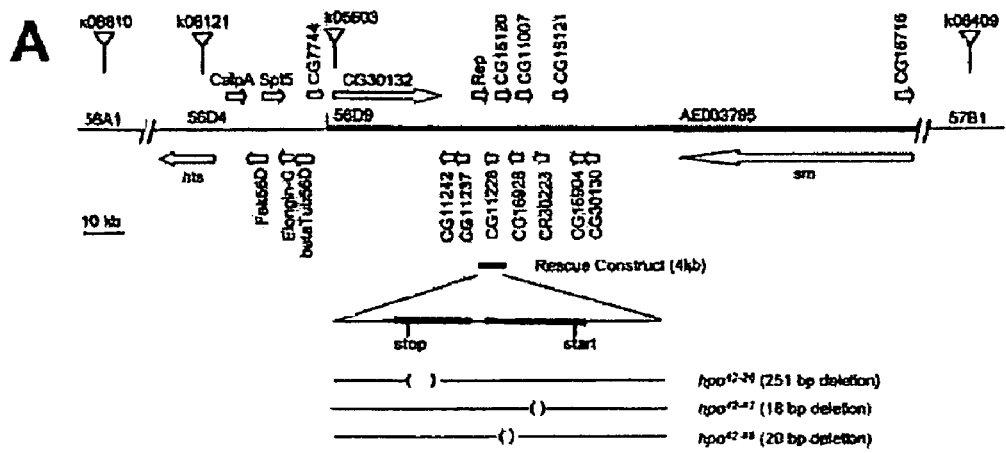
FIGS. 4A and 4B—Identification of the hpo gene.

Consistent with the cell death defects, elevated level of DIAP1 protein was detected in hpo mutant clones in pupal eyes (FIGS. 3C-3C") and third instar eye discs (FIGS. 3D-3D"). In third instar eye discs, elevated DIAP1 level is observed in all cells within the hpo mutant clones, irrespective of their differentiation status (FIGS. 3D-3D"). Thus, hpo acts cell-autonomously to down-regulate the level of DIAPI protein. To investigate whether the regulation of DIAPI is mediated by transcriptional or post-transcriptional mechanism, the inventor used an enhancer trap insertion into the diap1 locus called th$^{j5c8}$. This enhancer trap line carries a P[lacZ] insertion in the 5' untranslated region of diap1 (Hay et al., 1995) and its expression pattern mimics that of endogenous diap1 (Ryoo et al., 2002). Expression of the th$^{j5c8}$ P[lacZ] reporter was elevated in hpo mutant clones in a cell-autonomous manner (FIGS. 3E-3E"). A similar increase in th$^{j5c8}$ P[lacZ] reporter was also observed in hpo mutant clones in the wing discs (data not shown). The elevated level of diap1-lacZ is not due to increased stability of lacZ protein in hpo mutant cells, since expression of an unrelated P[lacZ] enhancer trap reporter was not affected in hpo mutant cells (FIGS. 3F-3F"). Quantification revealed that in hpo mutant cells, DIAP1 protein and diap1-lacZ reporter is 2.5 and 3.3-fold higher than that of wild-type cells, respectively. RT-PCR analysis confirmed an increase of diap1 transcript level in hpo mutant cells (see FIG. 5C). Thus it appears that hpo regulates diap1 largely through a transcriptional mechanism.

hpo encodes a Ser/Thr protein kinase of the Ste-20 family. Recombination mapping placed hpo between two P-elements: l(2)k08810 and l(2)k06409 (FIG. 4A). Male recombination mapping (Chen et al., 1998) further localized hpo distal to l(2)k06121 and l(2)k05603 (FIG. 4A). These two P-elements were also used for meiotic mapping. While one recombinant between hpo and l(2)k06121 was recovered from 500 events, none was recovered between hpo and l(2)k05603. These results suggest that hpo lies distal but close to l(2)kO5603. Starting from the insertion site of l(2)k05603, a series of contiguous DNA fragments were used to probe genomic DNA blots prepared from all hpo alleles. One fragment 40 kb away from l(2)k05603 revealed a polymorphism associated with hpo$^{42-20}$. Sequencing analysis revealed that hpo$^{42-20}$ contains a 251 bp deletion in the CG11228 gene. Analysis of genomic DNA from the remaining two hpo alleles revealed an 18 bp deletion in hpo$^{42-47}$ and 20 bp-deletion in hpo$^{42-48}$ in the predicted coding exons of CG11228 (FIG. 4A), suggesting that CG11228 corresponds to hpo. The inventor has thus renamed CG11228 as hpo.

hpo encodes a polypeptide with an N-terminal kinase domain and a non-catalytic C-terminal domain (FIG. 4B). Its kinase domain reveals Hpo as a member of the Ste20 family Ser/Thr kinases. The founding member of this family, Ste20, is a putative yeast mitogen-activated protein kinase kinase kinase (MAP4K) involved in the mating pathways. The Ste20 family kinases are further divided into the p21-activated kinases (PAK) and germinal center kinase (GCK) subfamilies. The overall architecture and catalytic domain sequence further places Hpo into the Group II GCK (Dan et al., 2001). Hpo is most closely related to human proteins MST2 (60% identity) and MST1 (58% identity). MST1 and MST2 were were first isolated based on their homology to yeast Ste20 (Creasy and Chernoff, 1995) and independently identified as kinases activated in NIH3T3 cells by extreme stress (Taylor et al., 1996). Little is known about the physiological function of MST2; however, several reports have shown that overexpression of MST1 promotes apoptosis and that MST1 itself is cleaved by caspases during apoptosis (Graves et al., 1998). Interestingly, the identified caspase cleavage site of MST1 (DEMD$^{326}$S, see FIG. 4B) is not conserved in Hpo. In particular, Hpo contains Glutamate instead of Serine immediately C-terminal to the putative caspase cleavage (FIG. 4B), and a S327E mutation of MST1 completely abolishes its cleavage by caspases (Glantschnig et al., 2002). Thus the *Drosophila* Hpo kinase is an improbable caspase substrate.

The molecular defects of the hpo alleles correlates with their overgrowth phenotype. hpo$^{42-47}$ causes an in-frame deletion of 6 residues (N166ILLNT$^{171}$) in kinase subdomain VI. N$^{166}$ is involved in ATP binding, and is one of the nine residues that are identical in all kinases (Hanks et al., 1988). Thus, hpo$^{42-47}$ is predicted a null allele. On the other hand, hpo$^{42-48}$ is predicted to delete most of the C-terminal non-catalytic domain of the Hpo, while hpo$^{42-20}$ deletes the last 91 residues at the C-terminus of Hpo. Thus, hpo$^{42-20}$ and hpo$^{42-48}$ are expected to be weaker alleles than hpo$^{42-47}$, a prediction that agrees with the phenotypic analyses of the hpo allelic series. A construct containing only the CG11228 locus was tested for its ability to rescue hpo mutant flies (FIG. 4A). Nine out of 10 independent transgenic lines tested fully rescued hpo$^{42-20}$, hpo$^{42-47}$ or hpo$^{42-48}$ homozygotes to wild-type adults, further confirming that hpo corresponds to CG11228. The remaining line, P[hpo]*, failed to rescue the lethality of hpo$^{42-47}$ or hpo$^{42-48}$, but partially rescued the lethality of hpo$^{42-20}$. 34% of hpo$^{42-20}$ homozygotes carrying a copy of P[hpo]* survived to adults with phenotypes such as held-out wings and mild overgrowth. As described later, this partially rescued genetic combination provides a sensitized genetic background to examine interactions with other components of the hpo pathway.

Figure 5:
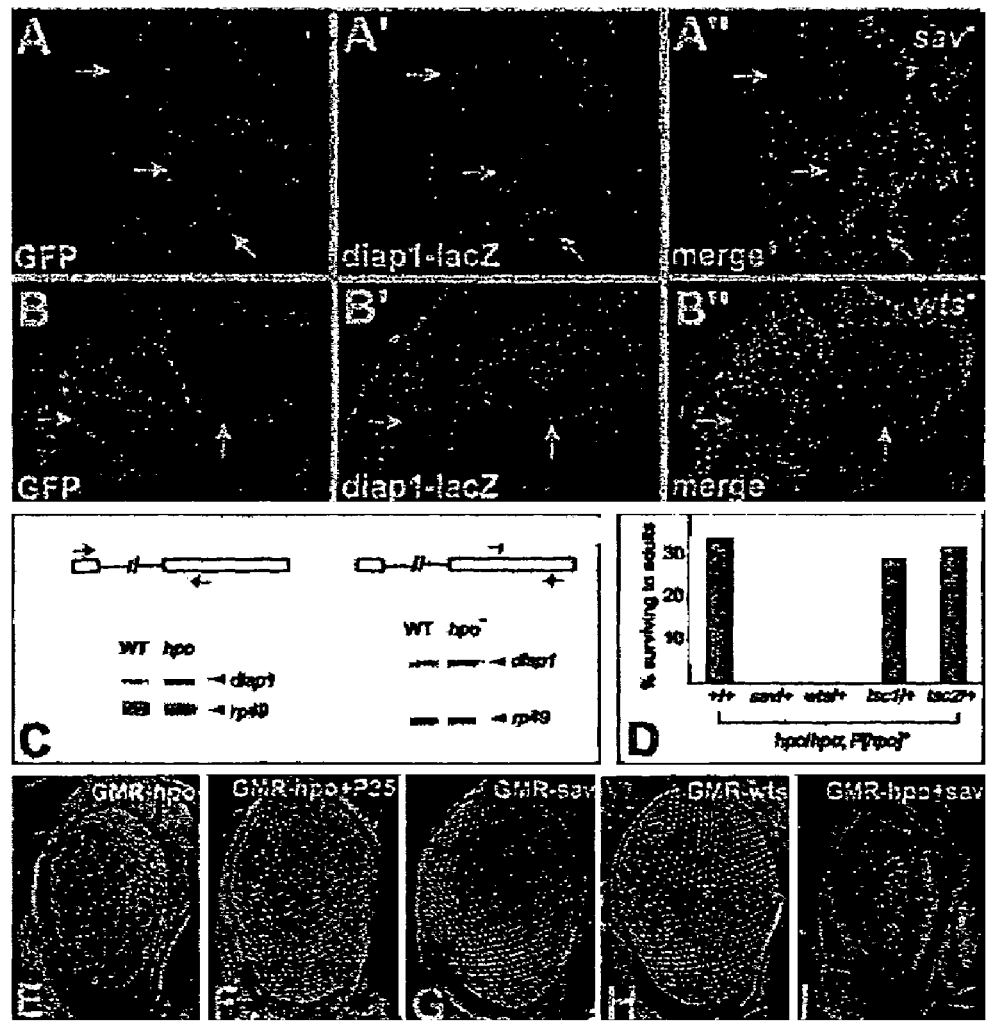
FIGS. 5A-I—Genetic interactions among hpo, sav and wts.

Genetic interaction among hpo, sav and wts. The cell cycle and apoptosis defects associated with hpo are similar to those described for sav and wts, including elevated cycE transcription, increased cell proliferation, and decreased cell death (Tapon et al., 2002). However, the results reported here differ significantly from the report of Tapon et al. (2002) regarding the mechanisms of DIAPI regulation by sav. While the inventor observed a clear upregulation of diap1 transcription in hpo mutant cells, it was reported that diap1 transcription is not affected in sav mutant cells. wts mutant clones were not analyzed in the previous report (Tapon et al., 2002). This discrepancy prompted us to re-evaluate sav mutant clones using the th$^{j5c8}$ enhancer trap as a readout for diap1 transcription. As shown in FIGS. 5A -5A", loss of sav clearly leads to upregulation of diap1 transcription. Tapon et al. (2002) used whole mount in situ hybridization to detect diap1 transcript without marking mutant clones, thus preventing a careful comparison of diap1 transcripts at high resolution. The inventor further examined mutant clones of wts using the th$^{j5c8}$ P[lacZ] reporter and observed a similar increase in diap1 transcription (FIGS. 5B-5B"). RT-PCR analysis revealed an increase in diap1 mRNA in hpo mutant larvae as compared to wild-type controls (FIG. 5C). Taken together, these data suggest that hpo, sav and wts likely function in a common signaling pathway that coordinately controls cell proliferation and apoptosis, at least partly through regulation of cycE and diap1 transcription.

To further probe the link between hpo, sav and wts, the inventor investigated their genetic interactions. As described earlier, hpo$^{42-20}$ homozygotes carrying a copy of P[hpo] * represents a sensitized genetic background in which hpo activity is compromised to a level that allows only a fraction of the animals to survive to adulthood. The inventor observed a dramatic genetic interaction between hpo and sav or wts in this genetic background. While 34% of hpo$^{42-20}$ homozygotes carrying a copy of P[hpo] * survive to adults, none of them survive to adulthood if these animals are simultaneously heterozygous for sav or wts (FIG. 5D). No genetic interactions were observed between hpo and tumor suppressor genes Tsc1 and Tsc2 (FIG. 5D).

To complement the above genetic analyses, the inventor created a gain-of-function genetic background for hpo and used it to examine genetic interactions between hpo, sav and wts. Overexpression of hpo using the GMR promoter results in a rough eye phenotype (FIG. 5E), which is largely suppressed by co-expression of cell death inhibitor P35 (FIG. 5F). As described previously, overexpression of sav by the GMR promoter has no effect (FIG. 5G), while overexpression of wts by the GMR promoter generates very subtle irregularities in ommatidial arrangement (FIG. 5H) (Tapon et al., 2002). Interestingly, co-expression of hpo and sav by the GMR promoter results in greatly reduced eye size (FIG. 5I), and co-expression of hpo and wts by the GMR promoter results in 100% lethality at early pupal stage. These genetic interactions further implicate hpo, sav and wts in a common signaling pathway.

Figure 6:
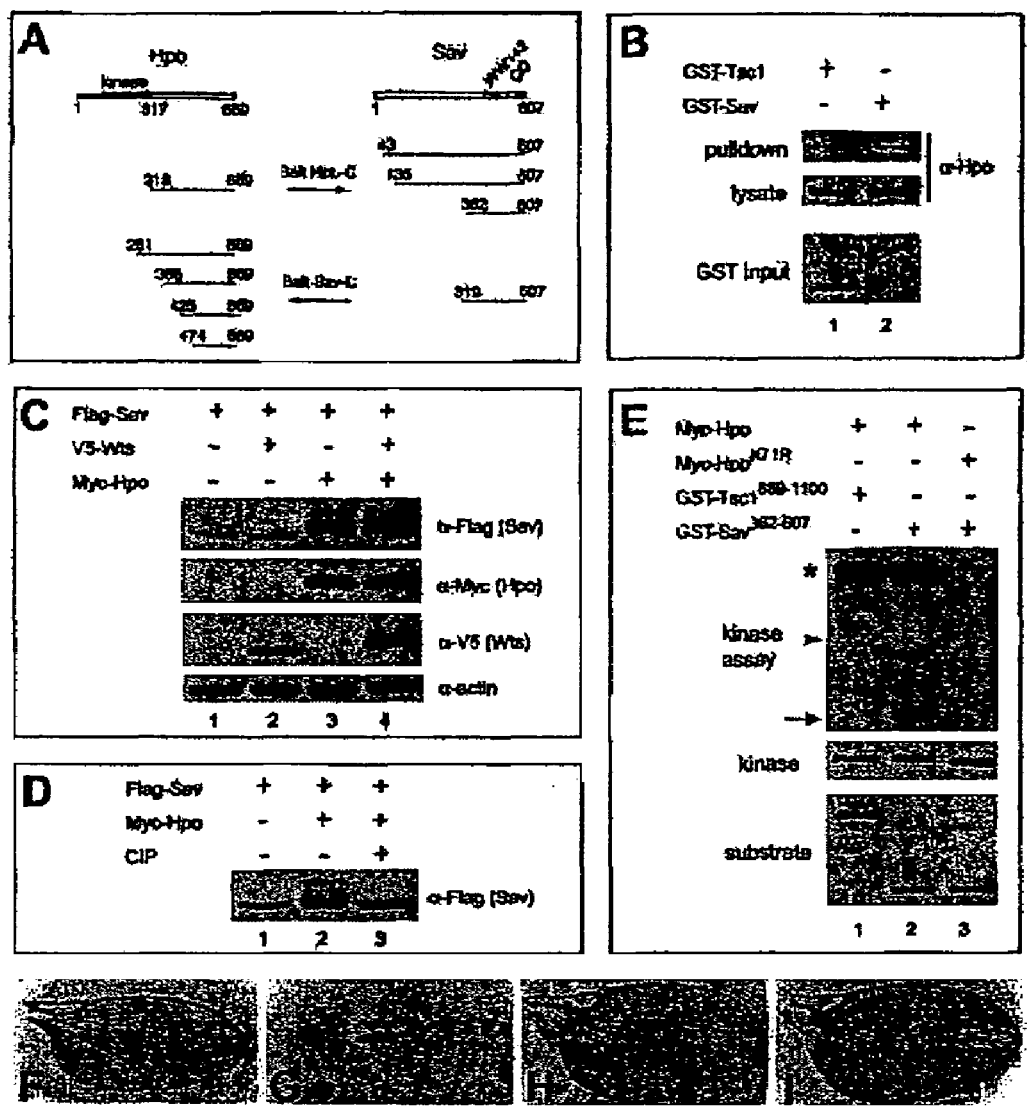
FIGS. 6A-I—Hpo binds to and phosphorylates Sav.

Hpo associates with and phosphorylates Sav. The inventor carried out a yeast two-hybrid screen in the hope of identifying Hpo-bindng proteins. The inventor screened approximately 1 million cDNA clones using as bait the non-catalytic C-terminal portion of Hpo (FIG. 6A). Interestingly, 6 out of 12 positive clones isolated from the screen corresponded to Sav, representing 3 different class of clones (FIG. 6A). These Hpo-interacting Sav clones define the C-terminal half of Sav (residue 362-607) as a Hpo-binding region. This region contains predicted Sav WW and coiled-coil domains (Tapon et al., 2002; Kango-Singh et al., 2002). The inventor carried out another yeast two-hybrid screen using the C-terminal half of Sav as the bait (FIG. 6A). In this screen, 5 out of 45 positive clones isolated from the screen corresponded to Hpo, representing 4 different class of clones (FIG. 6A). These Sav-interacting Hpo clones define the C-terminal portion of Hpo (residue 474-669) as a Sav-binding region. The identification of Hpo and Sav as interacting proteins in unbiased yeast two-hybrid screens provides strong evidence that these proteins interact with each other in vivo. Consistent with this hypothesis, Hpo and Sav associate with each other in vitro. As shown in FIG. 6B, GST fusion protein containing full-length Sav, but not a control GST fusion protein, was able to specifically pull down endogenous Hpo protein from S2 cell extracts. Hpo and Sav also interact with each other in co-immunoprecipitation assays (see FIG. 7E).

The inventor next investigated whether Hpo could function as a Sav kinase. For this purpose, the inventor established a co-transfection assay in S2 cells. As shown in FIG. 6C, co-expression of Hpo and Sav resulted in retarded mobility of Sav (compare lanes 1 and 3), leading to the formation of multiple slower migrating bands. Phosphatase treatment abrogated this shift (FIG. 6D), suggesting that the mobility shift is due to protein phosphorylation. On the other hand, co-expression of Sav and Wts, also a Ser/Thr kinase, did not result in Sav mobility shift (compare lanes 1 and 2), nor did expression of Wts affect the phosphorylation of Sav by Hpo (compare lanes 3 and 4). In vitro, myc-tagged Hpo protein specifically phosphorylated a GST fusion protein containing the Hpo-binding region of Sav (lane 2 in FIG. 6E), while no signals were detected using a control substrate or the kinase dead Hpo$^{K71R}$ mutant (lanes 1 and 3 of FIG. 6E). Thus, Hpo phosphorylates Sav.

The results presented above indicate a model wherein the C-terminal domain of Hpo associates with Sav and presents Sav to the Hpo kinase. If so, a kinase-dead mutant of Hpo, or the C-terminal non-catalytic domain of Hpo expressed alone, should behave as dominant negative forms, since these variants should associate non-productively with endogenous Sav and interfere with signal propagation. Indeed this is the case. While expression of wild-type Hpo using the wing-specific MS1096 Gal4 driver results in a dramatically reduced wing size (FIGS. 6F and 6G), expression of the kinase dead Hpo$^{K71R}$ mutant results in 35% increase in wing size (FIGS. 6F and 6H). Similarly, an increase (31%) in wing size is observed upon expression of Hpo$^{318-669}$, which contains just the C-terminal non-catalytic domain of Hpo (FIGS. 6F and 6I).

Figure 7:
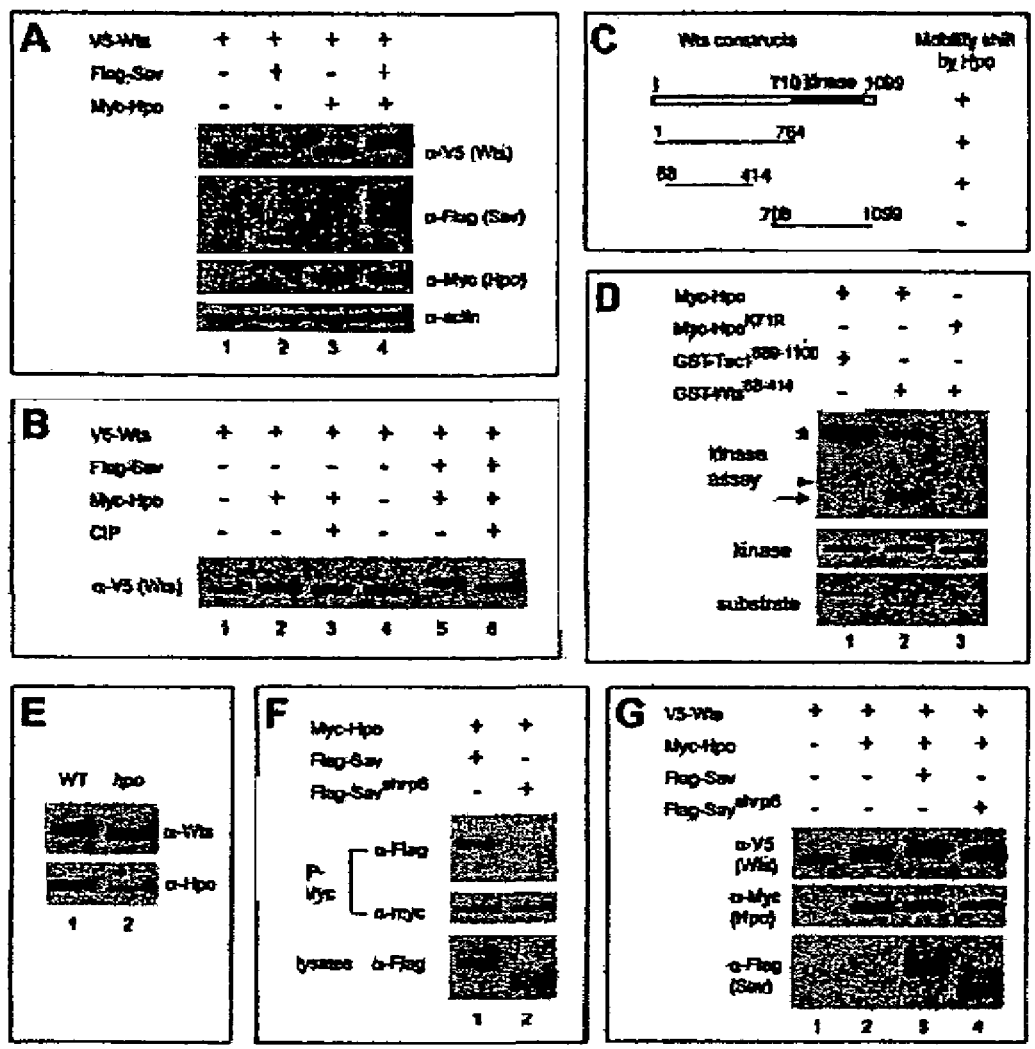
FIGS. 7A-G—Hpo/Sav interaction promotes Wts phosphorylation.

Hpo/Sav interaction promotes Wts phosphorylation. Having established a functional link between Hpo and Sav, and given the results from this genetic analyses implicating hpo, sav and wts in a common pathway, the inventor investigated whether Wts might be regulated by Hpo and/or Sav. In S2 cells, expression of Hpo results in retarded mobility of Wts, while coexpression of Hpo and Sav results in a further mobility shift of Wts (FIG. 7A). For simplicity, the inventor refers to this further shift of Wts upon coexpression of Hpo and Sav as "supershift" to be distinguished from the mobility shift caused by expression of Hpo alone. Both shifts were largely abolished by phosphatase treatment, confirming that the shifts were due to phosphorylation (FIG. 7B). Taken together, these data suggest that Sav increases the ability of Hpo to phosphorylate Wts.

The mobility shift assay described above allowed the inventor to narrow down the domain of Wts that is the target of Hpo-mediated phosphorylation to a region at the N-terminal non-catalytic portion (residues 68-414) of the Wts protein (FIG. 7C). In vitro, a GST fusion protein containing this region of Wts was phosphorylated by Hpo, while no signals were detected using a control substrate or the kinase dead Hpo$^{K71R}$ (FIG. 7D). Consistent with Wts as a kinase substrate of Hpo, the mobility of endogenous Wts protein on SDS-PAGE is increased in Hpo mutant animals (FIG. 7E).

The results indicate a model wherein Hpo associates with and phosphorylates Sav and interactions between Hpo and Sav facilitate Wts phosphorylation by Hpo. This model is consistent with previous report of direct physical interaction between Sav and Wts (Tapon et al., 2002). Thus, Sav could be viewed as an adaptor protein that brings Hpo in proximity to Wts to facilitate Wts phosphorylation. Since the Sav WW domains have been implicated in Sav/Wts interaction (Tapon et al., 2002), the inventor speculated that the coiled-coil domain of Sav, located C-terminal to the WW domains, might be involved in Sav/Hpo interaction (see FIG. 6A for schematics of Sav domains). Interestingly, the shrp6 allele of sav causes a frameshift mutation that truncates just the coiled-coil domain but leaves the WW domains intact (Kango-Singh et al., 2002). To pinpoint the functional defect of the sav$^{shrp6}$ allele, the inventor engineered a mutant Sav protein, Sav$^{shrp6}$, that lacks the C-terminal 79 residues as seen in sav$^{shrp6}$, and examined the ability of this mutant protein to associate with Hpo and to facilitate Wts phosphorylation by Hpo. Unlike wild-type Sav, Sav$^{shrp6}$ could not associate with Hpo (FIG. 7F), suggesting that the coiled-coil domain of Sav is required for Hpo/Sav interaction. Importantly, co-expression of Sav$^{shrp6}$ and Hpo could no longer cause the supershift of Wts as seen when wild-type Sav and Hpo are co-expressed (FIG. 7G). Thus, Hpo/Sav interaction is required for Sav to facilitate the phosphorylation of Wts by Hpo.

A human homologue of lipo rescues the overgrowth phenotype of Drosophila hipo mutants. Hpo encodes a Ste-20 family protein kinase whose closest relative in humans is MST2 (60% identity). To test the functional significance of the sequence conservation between Hpo and MST2 and to gain insights into the function of MST2, the inventor tested whether the overgrowth phenotype of Drosophila hpo mutant tissues could be rescued by expression of human MST2. The inventor introduced MST2 cDNA into Drosophila under the control of the hsp70 promoter. A 60 min heatshock pulse per day starting from the $2^{nd}$ instar larval stage until eclosion completely suppressed the overgrown-head phenotype associated eyeless-FLP-hpo$^{42-47}$ (FIGS. 8A-8D). The abnormal cell morphology phenotype was also completely rescued (compare FIGS. 8E and 8F). Taken together, these results reveal a high degree of functional conservation between Hpo and MST2 and suggest that MST2 plays a similar role in mammalian growth control.

Example 3

Discussion

The mechanisms of how body and organ size are regulated are largely unknown (Conlon and Raff, 1999). The final size of an organ or organism is a function of both cell size and cell number. Thus, size control in animal development is likely to involve a complex interplay of cell growth, proliferation and death. Recent studies in Drosophila have implicated a number of pathways in the control of cell growth and proliferation, including the Ras and Myc oncogenes, Cyclin D/cdk4, insulin/PI3K and TSC/TOR pathways (Stocker and Hafen, 2000; Johnston and Gallant, 2002). Less is known about the contribution of cell death to developmental size-control in Drosophila. Expression of P35 effectively blocks apoptosis in Drosophila, but has no detectable effects on the growth of imaginal disc cells (Neufeld et al., 1998), suggesting that blocking cell death alone is not sufficient to offset the "mass checkpoint" that dictates the final size of imaginal discs. One possibility is that reduced apoptosis is compensated by decreased cell proliferation. Thus, decreased cell death might have to be coupled with a concomitant increase in cell proliferation in order to offset the mass checkpoint. This hypothesis is supported by studies of sav, a tumor suppressor gene that negatively regulates CycE and DIAP1 levels (Tapon et al., 2002), and bantam, a microRNA that promotes cell proliferation as well as downregulates the proapoptotic gene hid (Brennecke et al., 2003). Such coupling between cell death and proliferation is also likely an important element in cancer. Indeed, it is believed that deregulated proliferation together with suppressed apoptosis forms an obligate and perhaps universal platform to support neoplastic progression (Green and Evan, 2002).

In this report, the inventor provides evidence that hpo represents an essential regulator of organ size through its dual roles in cell proliferation and apoptosis. Loss of hpo does not affect cell fate, but leads to increased cell proliferation and decreased apoptosis. A critical downstream effector of hpo in cell proliferation is cycE, whose transcription level is increased in hpo mutant cells. That cycE represents a critical downstream effector of hpo is consistent with previous studies implicating the CycE/cdk2 complex as a central regulator of cell cycle progression in Drosophila (Richardson et al., 1995; Neufeld et al., 1998). The present analyses further identify the cell death inhibitor diap1 as another downstream effector of hpo. In Drosophila, cell death molecules such as Reaper, Hid and Grim downregulate DIAP 1 activity through several posttranscriptional mechanisms, including direct binding, DLAP1 ubiquitination or a general inhibition of protein translation (reviewed in Martin, 2002). Unlike Reaper, Hid or Grim, Hpo appears to regulate DIAP1 largely through a transcriptional mechanism. To the inventor's knowledge, such a mode of DIAPI regulation has not been described previously in Drosophila. These studies also raise the intriguing possibility that jointly elevated CycE and IAP levels might represent a common pathway for tumor progression in humans.

Figure 8:
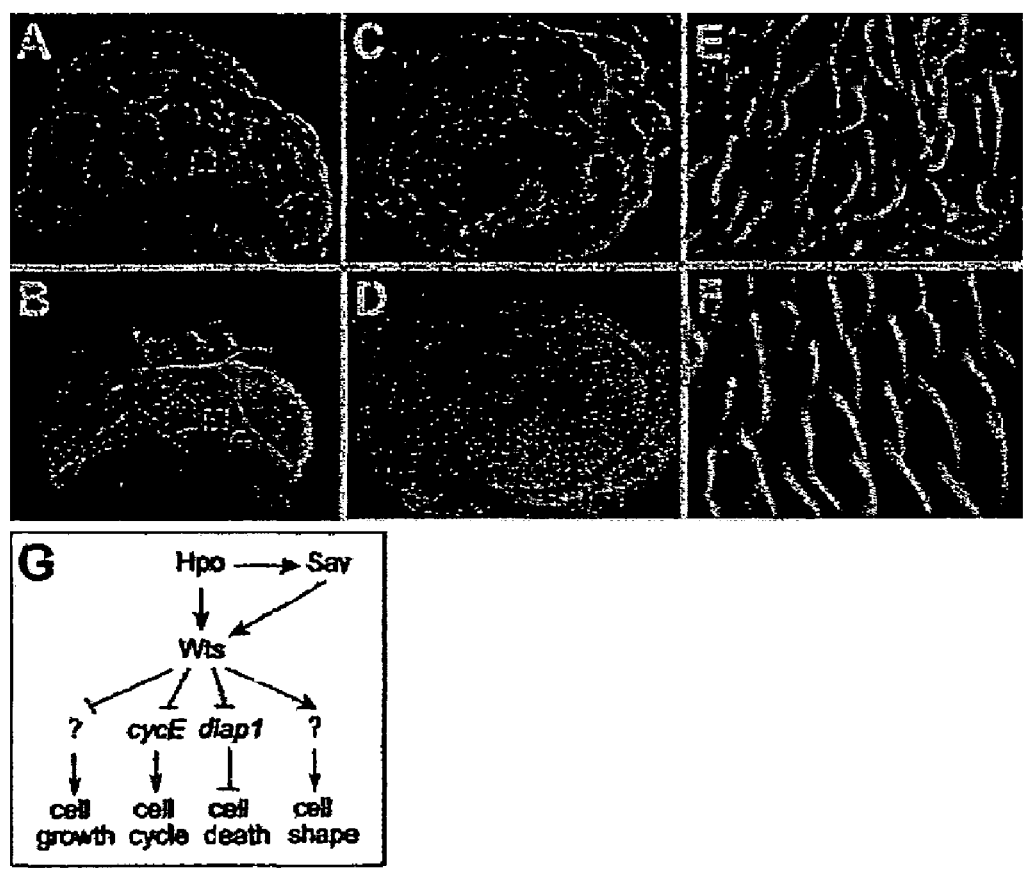
FIGS. 8A-G—A human homologue of hpo rescues the overgrowth phenotype of Drosophila hpo mutants.

While a great deal is yet to be learned about the mechanism of Hpo function in growth suppression, here the inventor has provided genetic and biochemical evidence that Sav and Wts are additional components of this emerging pathway (FIG. 8G). Hpo encodes a Ste-20 family Ser/Thr kinase that associates with and phosphorylates Sav. The Hpo/Sav interaction promotes the phosphorylation of Wts by Hpo. The biochemical interactions among Hpo, Sav and Wts are supported by the dosage-sensitive genetic interactions among these genes and the comparable upregulation of cycE and diap1 transcription in each of their mutant backgrounds. This model might explain why loss of wts results in the greatest overgrowth among the three genes, since it is the most downstream component among the three. Loss of wts might be expected to completely abolish the output of this pathway, while loss of hpo or sav might still leave Wts with some level of kinase activity. This model might also explain why sav mutations result in the least severe phenotype among the three, since Sav facilitates, but is not absolutely required for, the phosphorylation of Wts by Hpo. Besides cycE and diap1, additional effectors downstream of the Hpo pathway are likely to exist. The cell morphology phenotype, for example, is likely mediated by some unknown target(s) of this pathway. Indeed, protein kinases related to Wts have been implicated in cytoskeleton and cell shape regulation in S. pombe, Neurospora and C. elegans (Zallen et al., 2000 and references therein). In addition, there likely exist effector(s) of the Hpo pathway in cell growth, since cell growth must be proportionally stimulated to sustain the increased proliferation of hpo, sav or wts mutant cells.

The inventor proposes that Hpo, Sav and Wts define a tumor suppression pathway that coordinately regulates cell proliferation and apoptosis, and the Hpo-Sav-Wts pathway might be involved in tumorigenesis in mammals. Indeed, mice lacking a wts ortholog develop soft-tissue sarcomas and ovarian tumors (St John et al., 1999), and a human ortholog of wts is downregulated in a subset of soft tissue sarcomas (Hisaoka et al., 2002). In addition, the human ortholog of sav is mutated in several cancer cell lines (Tapon et al., 2002). While the role of hpo in human cancers is has not been thoroughly examine, the inventor shows here that Mst2, a human homologue of Hpo, completely rescues flies lacking hpo, revealing a high degree of functional conservation between flies and humans. It will be important to identify upstream regulators of the Hpo pathway, which might provide critical insights into the nature of the signal(s) that normally stop growth when a given organ reaches its characteristic size. The conservation of Hpo, Sav and Wts from *Drosophila* to humans suggest that such size-control mechanisms are likely universal to all animals.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. References

The following references, to the extent that they provide exemplary procedural or other details supplementary to those set forth herein, are specifically incorporated herein by reference:

U.S. Pat. No. 4,196,265
U.S. Pat. No. 4,683,195
U.S. Pat. No. 4,683,202
U.S. Pat. No. 4,800,159
U.S. Pat. No. 4,873,191
U.S. Pat. No. 4,879,236
U.S. Pat. No. 5,843,663
U.S. Pat. No. 5,849,481
U.S. Pat. No. 5,849,486
U.S. Pat. No. 5,851,772
U.S. Pat. No. 5,871,986
U.S. Pat. No. 5,900,481
U.S. Pat. No. 5,919,626
U.S. Pat. No. 5,928,906
U.S. Pat. No. 6,500,938
Almendro et al., *J. Immunol.*, 157(12):5411-5421, 1996.
Angel et al., *Mol. Cell. Biol.*, 7:2256, 1987.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1994.
Baichwal and Sugden, In: *Gene Transfer*, Kucherlapati (Ed.), New York, Plenum Press, 117-148, 1986.
Baneiji et al., *Cell*, 27(2 Pt 1):299-308, 1981.
Baneiji et al., *Cell*, 33(3):729-740, 1983.
Barany and Merrifield, In: *The Peptides*, Gross and Meienhofer (eds.), Academic Press, New York, 1-284, 1979.
Bellus, *J. Macromol. Sci. Pure Appl. Chem.*, A31(1): 1355-1376, 1994.
Benvenisty and Neshif, *Proc. Natl. Acad. Sci. USA*, 83(24): 9551-9555, 1986.
Berkhout et al., *Cell*, 59:273-282, 1989.
Blanar et al, *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brennecke et al., *Cell*, 113:25-36., 2003.
Brinster et al., *Proc. Natl. Acad. Sci. USA*, 82(13):4438-4442, 1985.
Bulla and Siddiqui, *J. Virol.*, 62:1437, 1986.
Bystryn et al., *Cancer Res.*, 45(11 Pt 2):5603-5607, 1985.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Capaldi et al., *Biochem. Biophys. Res. Comm.*, 76:425, 1977.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chattejee et al., *Proc. Natl. Acad. Sci. USA*, 86:9114, 1989.
Chen and Okayama, *Mol. Cell Biol.*, 7(8):2745-2752, 1987.
Chenetal., *Genetics*, 149:157-163, 1998.
Choi et al., *Cell*, 53:519, 1988.
Coffin, In: *Virology*, Fields et al., eds., Raven Press, N.Y., 1437-1500, 1990.
Cohen et al., *J. Cell. Physiol.*, 5:75, 1987.
Conlon and Raff, *Cell*, 96:235-244, 1999.
Costa et al., *Mol. Cell. Biol.*, 8:81, 1988.
Coupar et al., *Gene*, 68:1-10, 1988.
Creasy and Chemoff, *J. Biol. Chem.*, 270:21695-21700, 1995.
Cripe et al., *EMBO J.*, 6:3745, 1987.
Culotta and Hamer, *Mol. Cell. Biol.*, 9:1376, 1989.
Dan et al., *Trends Cell Biol.*, 11:220-230, 2001.
Dandolo et al., *J. Virology*, 47:55-64, 1983.
De Villiers et al., *Nature*, 312(5991):242-246, 1984.
Deschamps et al., *Science*, 230:1174-1177, 1985.
Dubenskyetal., *Proc. Natl. Acad. Sci. USA*, 81:7529-7533, 1984.
Duman-Scheel et al., *Nature*, 417:299-304, 2002.
Edbrooke et al., *Mol. Cell. Biol.*, 9:1908, 1989.
Edlund et al., *Science*, 230:912-916, 1985.
Elder et al., *Cancer Res.*, 49:5091-5096, 1989.
European Pat. No. Appl. EP 0273085
Fechheimer et al., *Proc. Natl. Acad. Sci. USA*, 84:8463-8467, 1987.
Feng and Holland, *Nature*, 334:6178, 1988.
Ferkol et al., *FASEB J.*, 7:1081-1091, 1993.
Fidler and Hart, *Science*, 217:998-1001, 1982.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Freifelder, In: *Physical Biochemistry Applications to Biochemistry and Molecular Biology*, 2nd ed. Wm. Freeman and Co., New York, N.Y., 1982.
Friedmann, *Science*, 244:1275-1281, 1989.
Fujita et al., *Cell*, 49:357, 1987.
Gao and Pan, *Genes Dev.*, 15:1383-1392, 2001.
Ghosh and Bachhawat, In: *Liver Diseases, Targeted Diagnosis and Therapy Using Specific Receptors and Ligands*, Wu et al. (Eds.), Marcel Dekker, N.Y., 87-104, 1991.
Gilles et al., *Cell*, 33:717, 1983.
Glantschnig et al., *J. Biol. Chem.*, 277:42987-42996, 2002.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.

Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Graham and Prevec, *Biotechnology*, 20:363-390, 1992.
Graham and Van Der Eb, *Virology*, 52:456-467, 1973.
Graham et al, *J. General Virology*, 36:59-74, 1977.
Graves et al., *EMBO J.*, 17:2224-2234, 1998.
Green and Evan, *Cancer Cell*, 1:19-30, 2002.
Greene et al., *Immunology Today*, 10:272, 1989
Grosschedl and Baltimore, *Cell*, 41:885, 1985.
Grunhaus et al., *Seminar in Virology*, 200(2):535-546, 1992.
Hanks et al., *Science*, 241:42-52, 1988.
Harland and Weintraub, *J. Cell Biol.*, 101:1094-1099, 1985.
Harlow and Lane, Antibodies: A Laboratory Manual. Cold Spring Harbor Laboratory Press, Cold Spring harbor, N.Y., 553-612, 1988.
Haslinger and Karin, *Proc. Natl. Acad. Sci. USA*, 82:8572, 1985.
Hauber and Cullen, *J. Virology*, 62:673, 1988.
Hay et al., *Cell*, 83:1253-1262, 1995.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Herz and Gerard, *Proc. Natl. Acad. Sci. USA*, 90:2812-2816, 1993.
Higuchi et al., *Biotechnology*, 11(9):1026-1030, 1993.
Hirochika et al., *J. Virol.*, 61:2599, 1987.
Hirsch et al., *Mol. Cell. Biol.*, 10:1959, 1990.
Hogan et al., In: *Manipulating the Mouse Embryo*: A Laboratory Manual, 2nd ed.,Cold Spring Harbor Laboratory Press, 1994.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *PCR Protocols*, Academic Press, Inc., San Diego Calif., 1990.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Justice et al., *Genes Dev.*, 9:534-546, 1995.
Kadesch and Berg, *Mol. Cell. Biol.*, 6:2593, 1986.
Kaneda et al., *Science*, 243:375-378, 1989.
Kango-Singh et al., *Development*, 129:5719-5730, 2002.
Karin et al., *Mol. Cell. Biol.*, 7:606, 1987.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kraus et al. *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Lareyre et al., *J. Biol Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988-990, 1993.
Lee et al., *Biochem. Biophys. Res. Commun.*, 240(2):309-313, 1997.
Lee et al., *Nature*, 294:228, 1981.
Lee et al., *Nucleic Acids Res.*, 12:4191-206, 1984.
Levinson et al., *Nature*, 295:79, 1982.
Levrero et al., *Gene*, 101:195-202, 1991.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1988.
Mann et al., *Cell*, 33:153-159, 1983.
Martin, *Cell*, 109:793-796, 2002.
McNeall et al., *Gene*, 76:81, 1989.
Merrifield, *Science*, 232:341-347, 1986.
Miksicek et al., *Cell*, 46:203, 1986.
Mordacq and Linzer, *Genes and Dev.*, 3:760, 1989.
Moreau et al., *Nuc. Acids Res.*, 9:6047, 1981.
Morton et al., *Cancer*, 71:3737-3743, 1993.
Muesing et al., *Cell*, 48:691, 1987.
Neufeld et al., *Cell*, 93:1183-1193, 1998.
Newsome et al., *Development*, 127:851-860, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Nowell, In: *Tumor Cell Heterogeneity*, Owens et al. (Eds.), NY, Academic Press, 351-365, 1982.
Ondek et al., *EMBO J.*, 6:1017, 1987.
Ornitz et al., *Mol. Cell. Biol.*, 7:3466, 1987.
Palmiter et al., *Nature*, 300:611, 1982.
Pan and Rubin, *Cell*, 90:271-280, 1997.
Paskind et al., *Virology*, 67:242-248, 1975.
PCT Application WO 90/07641
Pech et al., *Mol. Cell. Biol.*, 9:396, 1989.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffiner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn al., *Mol. Cell. Biol.*, 9:4713, 1989.
Ragot et al., *Nature*, 361:647-650, 1993.
Redondo et al., *Science*, 247:1225, 1990.
Reisman and Rotter, *Mol. Cell. Biol.*, 9:3571, 1989.

Remington's Pharmaceutical Sciences, 15th ed., 33:624-652, Mack Publishing Company, Easton, Pa., 1980
Resendez Jr. et al., *Mol. Cell. Biol.,* 8:4579, 1988.
Rich et al., *Hum. Gene Ther.,* 4:461-476, 1993.
Richardson et al., *Development,* 121:3371-3379, 1995.
Ridgeway, In: *Vectors: A survey of molecular cloning vectors and their uses,* Rodriguez and Denhardt (Eds.), Stoneham: Butterworth, 467-492, 1988.
Ripe et al., *Mol. Cell. Biol.,* 9:2224, 1989.
Rippe et al., *Mol. Cell Biol.,* 10:689-695, 1990.
Rittling et al., *Nuc. Acids Res.,* 17:1619, 1989.
Rosen et al., *Cell,* 41:813, 1988.
Rosenfeld et al., *Cell,* 68:143-155, 1992.
Rosenfeld et al., *Science,* 252:431-434, 1991.
Ryoo et al., *Nat. Cell Biol.,* 4:432-438, 2002.
Sakai et al., *Genes and Dev.,* 2:1144, 1988.
Sambrook et al., Cold Spring Harbor Laboratory, old Spring Harbor, N.Y., 1989.
Satake et al., *J. Virology,* 62:970, 1988.
Schaffner et al., *J. Mol. Biol.,* 201:81, 1988.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
St John et al., *Nat. Genet.,* 21:182-186, 1999.
Stephens and Hentschel, *Biochem. J.,* 248:1, 1987.
Stewart and Young, Solid Phase Peptide Synthesis, 2d. ed., Pierce Chemical Co., 1984.
Stocker and Hafen, *Curr. Opin. Genet. Dev.,* 10:529-535, 2000.
Stratford-Perricaudet and Perricaudet, In: *Human Gene Transfer,* Eds, Cohen-Haguenauer and Boiron, John Libbey Eurotext, France, 51-61, 1991.
Stratford-Perricaudet et al, *Hum. Gene. Ther.,* 1:241-256, 1990.
Stuart et al., *Nature,* 317:828, 1985.
Sullivan and Peterlin, *Mol. Cell. Biol.,* 7:3315, 1987.
Swartzendruber and Lehman, *J. Cell. Physiology,* 85:179, 1975.
Takebe et al., *Mol. Cell. Biol.,* 8:466, 1988.
Tam et al., *J. Am. Chem. Soc.,* 105:6442, 1983.
Tapon et al., *Cell,* 110:467-478, 2002.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Taylor et al., *Proc. Natl. Acad. Sci. USA,* 93:10099-10104, 1996.
Temin, In: *Gene Transfer,* Kucherlapati (Ed.), NY, Plenum Press, 149-188, 1986.
Thiesen et al., *J. Virology,* 62:614, 1988.
Treisman, *Cell,* 42:889, 1985.
Tronche et al., *Mol. Biol. Med.,* 7:173, 1990.
Trudel and Constantini, *Genes and Dev.* 6:954, 1987.
Tsumaki et al., *J. Biol. Chem.,* 273(36):22861-22864, 1998.
Tur-Kaspa et al., *Mol. Cell Biol.,* 6:716-718, 1986.
Tyndell et al., *Nuc. Acids. Res.,* 9:6231, 1981.
Vannice and Levinson, *J. Virology,* 62:1305, 1988.
Vasseur et al., *Proc Natl. Acad. Sci. U.S.A.,* 77:1068, 1980.
Wagner et al., *Proc. Natl. Acad. Sci. USA* 87(9):3410-3414, 1990.
Wang and Calame, *Cell,* 47:241, 1986.
Weber et al., *Cell,* 36:983, 1984.
Weinberger et al. *Mol. Cell. Biol.,* 8:988, 1984.
Winoto and Baltimore, *Cell* 59:649, 1989.
Wolff and Ready, In: *The development of Drosophila melanogaster,* Bate and Martinez Arias (Eds.), NY, Cold Spring Harbor Laboratory Press, 1277-1325, 1993.
Wong et al., *Gene,* 10:87-94, 1980.
Wu and Wu, *Adv. Drug Delivery Rev.,* 12:159-167, 1993.
Wu and Wu, *Biochemistry,* 27:887-892, 1988.
Wu and Wu, *J. Biol. Chem.,* 262:4429-4432, 1987.
Wu et al., *Biochem. Biophys. Res. Commun.,* 233(1):221-6, 1997.
Xu et al., *Development,* 121:1053-1063, 1995.
Yang and Russell, *Proc. Natl. Acad. Sci. USA,* 87:4144-4148, 1990.
Yoo et al., *Nat. Cell Biol.,* 4:416-424, 2002.
Yutzey et al. *Mol. Cell. Biol.,* 9:1397, 1989.
Zallen et al., *Mol. Biol. Cell,* 11:3177-3190, 2000.
Zelenin et al., *FEBS Lett.,* 280:94-96, 1991.
Zhao-Emonet et al., *Biochim. Biophys. Acta,* 1442(2-3):109-119, 1998.

---

I claim:

1. A primary tumor cancer cell comprising an expression cassette comprising a polynucleotide encoding a polypeptide having the sequence of SEQ ID NO:2, wherein said polynucleotide is under the control of a promoter operable in eukaryotic cells, said promoter being heterologous to said polynucleotide.

2. The primary tumor cancer cell of claim 1, wherein said promoter is a tissue specific promoter.

3. The primary tumor cancer cell of claim 1, wherein said promoter is an inducible promoter.

4. The primary tumor cancer cell of claim 1, wherein said expression cassette further comprises a polyadenylation signal.

5. The primary tumor cancer cell of claim 1, wherein said expression cassette is comprised in a viral vector.

6. The primary tumor cancer cell of claim 1, wherein said expression cassette is comprised in a non-viral vector.

7. The primary tumor cancer cell of claim 1, wherein the cell is derived from a primary tumor selected from the group consisting of brain tumor, lung tumor, liver tumor, spleen tumor, kidney tumor, lymph node tumor, small intestine tumor, blood cell tumor, pancreatic tumor, colon tumor, stomach tumor, cervix tumor, breast tumor, endometrial tumor, prostate tumor, testicle tumor, ovarian tumor, skin tumor, head and neck tumor, esophageal tumor, oral tissue tumor, and bone marrow tumor.

8. The primary tumor cancer cell of claim 5, wherein said viral vector is selected from the group consisting of a retroviral vector, an adenoviral vector, an adeno-associated viral vector, a vaccinia viral vector, and a herpesviral vector.

* * * * *

SEQUENCE LISTING

<160> NUMBER OF SEQ ID NOS: 4

<210> SEQ ID NO 1
<211> LENGTH: 2514
<212> TYPE: DNA
<213> ORGANISM: Drosophila hippo

<400> SEQUENCE: 1

```
aataaagaac aaaagtgtga tatgtcgctg tgaatagcca attatctgtg ttttctcgtg      60
ctaaatcaga aaattttcg caatgtctga gccagaggtg accagcgttg tagatatgaa      120
atcgcccaac atatcctcct cctgctcctt cttcaagctg aagaagctgt cggaggagtc      180
gcttctgcag ccgccggaaa aggtcttcga cattatgtac aagctgggcg agggcagcta      240
tggatcagtc tacaaggcag tgcacaagga aagcagctcc attgtggcca tcaagctggt      300
gccggtggag tccgacctgc acgagattat taaggagata tccattatgc aacaatgcga      360
```

```
ctcgccgtat gtggtgcgct attacggctc ctacttcaag cagtatgacc tgtggatctg    420
catggagtac tgtggcgccg gcagcgtctc cgacattatg cgtctgcgca aaaagacgct    480
gacggaggac gagatagcca ctattctgtc ggacactctg cagggcttgg tctatctgca    540
tctgcgtcgc aagatccatc gcgacatcaa ggcggccaac atcctgctca ataccgaagg    600
ctatgctaag ttggccgatt tcggagtcgc tggtcagctc acggacacaa tggccaagag    660
aaacactgtg atcggaacgc ccttctggat ggcccccgag gtgattgagg agattggcta    720
cgactgtgtg gcagacatat ggtcattggg catcaccgcc ttggaaatgg ccgagggaaa    780
gcccccatac ggtgagatcc atcccatgcg agccatcttt atgattccgc agaagccacc    840
accatcgttc cggaaccgga tcgctggagc acagagttcc attgacttcg tgagcaagtg    900
cctggtaaag gagccagacg accgggcaac ggccactgaa ctgctggagc acgagttcat    960
acgcaacgcc aagcaccgat cgatcctaaa gcctatgctt gaggagacct gtgccattcg   1020
cgagcagcaa cgcgccaatc gcagttttgg gggcgtgttg gctgctagtc aggcgaagag   1080
cttggcaacc caggaaaacg gaatgcaaca acacatcacg gacaacgcgt ttatggagga   1140
tccaggtact ctggtgccgg agaagttcgg tgaataccaa cagagctcag cctcagatgc   1200
caccatgata gcgcatgcag agcaaggtgt ggatgagggc actttgggc cgggtggact   1260
aaggaacctg tccaaggcag ctgctcctgc agcggcctct tcggcagcat ctcctctgga   1320
catgccggca gttgacagcg gcacaatggt ggagctggag tcgaacttgg gcactatggt   1380
aatcaactcc gattcggacg actccacaac ggccaaaaac aacgacgacc agaagccgcg   1440
aaaccgctac aggccgcagt tcctggagca cttcgatcgc aaaaatgcgg gagatggccg   1500
tggcgatgaa aaacccatag ccacagagta ttctccggca gcagcggagc agcaacaaca   1560
acaacaacag cagcagcaac aacaacagca ggatgaacag catctggcaa gcggggccaa   1620
cgatttgaac aactgggagc acaacatgga aatgcagttc cagcagatct ccgccattaa   1680
tcagtatggt ctgcagcagc accagcagca gcagcaagtt ctgatggctt atcccctgat   1740
gaacgaacaa ctcatcgcgc tcaacaatca accgaatctg ctgctcagca acgctgcgcc   1800
aatgggacag cagggaatac cggcagcggc tccagctcaa ccgccgcccg catatcagaa   1860
tcagcatatg catacgcaat cgcacgccta tgttgagggt gagtttgagt tcctcaagtt   1920
ccttaccttc gacgatctga accagcggct gtgcaacatc gatcacgaaa tggagctgga   1980
gatcgaacag ctaaacaaga aatacaatgc caagcggcag ccaattgttg acgccatgaa   2040
tgcaaagcgc aaacgccagc agaacatcaa taataatctg attaagatat aggtaaagca   2100
actcacaatt tcgcaagaca actgattatg aaatctcaac tcactcaatt gcctctacat   2160
tgggttaagt ttgcagatga atactgaatc ttacagaccc atcatctgta tcctctagaa   2220
attattcgtg cattgtgcaa atttaacctg gtggaagggt ctaaaatcaa tcacaagaaa   2280
tgaaaacaca aaagctttat tgtaaaatgc agtgaaaaca gaaagagga gtcatcggca    2340
gtatcttcca gcacgaaagc atattttctg ttagatttca tcaaatttat gcttggtttc   2400
ttatatccta gctttcattg atctgtcttt taatataaat aggtatgctc gaataaaatt   2460
tatcttgcgt ttattgtaaa aaaaaaaaa aaaaaaaaa aaaaaaaaa aaaa            2514
```

<210> SEQ ID NO 2
<211> LENGTH: 669
<212> TYPE: PRT
<213> ORGANISM: Drosophila hippo

<400> SEQUENCE: 2

```
Met Ser Glu Pro Glu Val Thr Ser Val Val Asp Met Lys Ser Pro Asn
 1               5                  10                  15

Ile Ser Ser Ser Cys Ser Phe Phe Lys Leu Lys Lys Leu Ser Glu Glu
            20                  25                  30

Ser Leu Leu Gln Pro Pro Glu Lys Val Phe Asp Ile Met Tyr Lys Leu
        35                  40                  45

Gly Glu Gly Ser Tyr Gly Ser Val Tyr Lys Ala Val His Lys Glu Ser
    50                  55                  60

Ser Ser Ile Val Ala Ile Lys Leu Val Pro Val Glu Ser Asp Leu His
65                  70                  75                  80

Glu Ile Ile Lys Glu Ile Ser Ile Met Gln Gln Cys Asp Ser Pro Tyr
                85                  90                  95

Val Val Arg Tyr Tyr Gly Ser Tyr Phe Lys Gln Tyr Asp Leu Trp Ile
            100                 105                 110

Cys Met Glu Tyr Cys Gly Ala Gly Ser Val Ser Asp Ile Met Arg Leu
        115                 120                 125

Arg Lys Lys Thr Leu Thr Glu Asp Glu Ile Ala Thr Ile Leu Ser Asp
130                 135                 140

Thr Leu Gln Gly Leu Val Tyr Leu His Leu Arg Arg Lys Ile His Arg
145                 150                 155                 160

Asp Ile Lys Ala Ala Asn Ile Leu Leu Asn Thr Glu Gly Tyr Ala Lys
                165                 170                 175

Leu Ala Asp Phe Gly Val Ala Gly Gln Leu Thr Asp Thr Met Ala Lys
            180                 185                 190

Arg Asn Thr Val Ile Gly Thr Pro Phe Trp Met Ala Pro Glu Val Ile
        195                 200                 205

Glu Glu Ile Gly Tyr Asp Cys Val Ala Asp Ile Trp Ser Leu Gly Ile
    210                 215                 220

Thr Ala Leu Glu Met Ala Glu Gly Lys Pro Pro Tyr Gly Glu Ile His
225                 230                 235                 240

Pro Met Arg Ala Ile Phe Met Ile Pro Gln Lys Pro Pro Pro Ser Phe
                245                 250                 255

Arg Glu Pro Asp Arg Trp Ser Thr Glu Phe Ile Asp Phe Val Ser Lys
            260                 265                 270

Cys Leu Val Lys Glu Pro Asp Arg Ala Thr Ala Thr Glu Leu Leu
        275                 280                 285

Glu His Glu Phe Ile Arg Asn Ala Lys His Arg Ser Ile Leu Lys Pro
    290                 295                 300

Met Leu Glu Glu Thr Cys Ala Ile Arg Glu Gln Gln Arg Ala Asn Arg
305                 310                 315                 320

Ser Phe Gly Gly Val Leu Ala Ala Ser Gln Ala Lys Ser Leu Ala Thr
                325                 330                 335

Gln Glu Asn Gly Met Gln His Ile Thr Asp Asn Ala Phe Met Glu
            340                 345                 350

Asp Pro Gly Thr Leu Val Pro Glu Lys Phe Gly Glu Tyr Gln Gln Ser
        355                 360                 365

Ser Ala Ser Asp Ala Thr Met Ile Ala His Ala Glu Gln Gly Val Asp
    370                 375                 380

Glu Gly Thr Leu Gly Pro Gly Gly Leu Arg Asn Leu Ser Lys Ala Ala
385                 390                 395                 400

Ala Pro Ala Ala Ala Ser Ser Ala Ala Ser Pro Leu Asp Met Pro Ala
                405                 410                 415
```

```
Val Asp Ser Gly Thr Met Val Glu Leu Glu Ser Asn Leu Gly Thr Met
            420                 425                 430

Val Ile Asn Ser Asp Ser Asp Asp Ser Thr Thr Ala Lys Asn Asn Asp
            435                 440                 445

Asp Gln Lys Pro Arg Asn Arg Tyr Arg Pro Gln Phe Leu Glu His Phe
            450                 455                 460

Asp Arg Lys Asn Ala Gly Asp Gly Arg Gly Asp Glu Lys Pro Ile Ala
465                 470                 475                 480

Thr Glu Tyr Ser Pro Ala Ala Ala Glu Gln Gln Gln Gln Gln Gln Gln
                485                 490                 495

Gln Gln Gln Gln Gln Gln Gln Asp Glu Gln His Leu Ala Ser Gly Ala
            500                 505                 510

Asn Asp Leu Asn Asn Trp Glu His Asn Met Glu Met Gln Phe Gln Gln
            515                 520                 525

Ile Ser Ala Ile Asn Gln Tyr Gly Leu Gln Gln His Gln Gln Gln Gln
            530                 535                 540

Gln Val Leu Met Ala Tyr Pro Leu Met Asn Glu Gln Leu Ile Ala Leu
545                 550                 555                 560

Asn Asn Gln Pro Asn Leu Leu Leu Ser Asn Ala Ala Pro Met Gly Gln
                565                 570                 575

Gln Gly Ile Pro Ala Ala Ala Pro Ala Gln Pro Pro Ala Tyr Gln
            580                 585                 590

Asn Gln His Met His Thr Gln Ser His Ala Tyr Val Glu Gly Glu Phe
            595                 600                 605

Glu Phe Leu Lys Phe Leu Thr Phe Asp Asp Leu Asn Gln Arg Leu Cys
            610                 615                 620

Asn Ile Asp His Glu Met Glu Leu Glu Ile Glu Gln Leu Asn Lys Lys
625                 630                 635                 640

Tyr Asn Ala Lys Arg Gln Pro Ile Val Asp Ala Met Asn Ala Lys Arg
                645                 650                 655

Lys Arg Gln Gln Asn Ile Asn Asn Asn Leu Ile Lys Ile
            660                 665

<210> SEQ ID NO 3
<211> LENGTH: 2820
<212> TYPE: DNA
<213> ORGANISM: Homo sapiens
<220> FEATURE:
<221> NAME/KEY: CDS
<222> LOCATION: (139)..(1614)

<400> SEQUENCE: 3
ccgcggagtt acgggaaagt tggtccgagt tcccagagtt tccctctgtg gtgccctagg      60
cttcggcccg gtgccccggc tcctttcctc ctttcggcct tcgccgtcca ccaggtccct     120
ctctctgtcc cggccgcc atg gag cag ccg ccg gcg cct aag agt aaa cta       171
                    Met Glu Gln Pro Pro Ala Pro Lys Ser Lys Leu
                     1               5                  10 aaa aag ctg agt gaa gac agt ttg act aag cag cct gaa gaa gtt ttt       219
Lys Lys Leu Ser Glu Asp Ser Leu Thr Lys Gln Pro Glu Glu Val Phe
             15                  20                  25 gat gta tta gag aag ctt gga gaa ggg tct tat gga agt gta ttt aaa       267
Asp Val Leu Glu Lys Leu Gly Glu Gly Ser Tyr Gly Ser Val Phe Lys
         30                  35                  40 gca ata cac aag gaa tcc ggt caa gtt gtc gca att aaa caa gta cct       315
Ala Ile His Lys Glu Ser Gly Gln Val Val Ala Ile Lys Gln Val Pro
     45                  50                  55
```

-continued

| | | |
|---|---|---|
| gtt gaa tca gat ctt cag gaa ata atc aaa gaa att tcc ata atg cag<br>Val Glu Ser Asp Leu Gln Glu Ile Ile Lys Glu Ile Ser Ile Met Gln<br>60                        65                          70                       75 | 363 |
| caa tgt gac agc cca tat gtt gta aag tac tat ggc agt tat ttt aag<br>Gln Cys Asp Ser Pro Tyr Val Val Lys Tyr Tyr Gly Ser Tyr Phe Lys<br>                      80                      85                        90 | 411 |
| aat aca gac ctc tgg att gtt atg gag tac tgt ggc gct ggc tct gtc<br>Asn Thr Asp Leu Trp Ile Val Met Glu Tyr Cys Gly Ala Gly Ser Val<br>                      95                      100                       105 | 459 |
| tca gac ata att aga tta cga aac aag aca tta ata gaa gat gaa att<br>Ser Asp Ile Ile Arg Leu Arg Asn Lys Thr Leu Ile Glu Asp Glu Ile<br>110                      115                      120 | 507 |
| gca acc att ctt aaa tct aca ttg aaa gga cta gaa tat ttg cac ttt<br>Ala Thr Ile Leu Lys Ser Thr Leu Lys Gly Leu Glu Tyr Leu His Phe<br>125                      130                      135 | 555 |
| atg aga aaa ata cac aga gat ata aaa gct gga aat att ctc ctc aat<br>Met Arg Lys Ile His Arg Asp Ile Lys Ala Gly Asn Ile Leu Leu Asn<br>140                      145                      150                      155 | 603 |
| aca gaa gga cat gca aaa ttg gca gat ttt gga gtg gct ggt cag tta<br>Thr Glu Gly His Ala Lys Leu Ala Asp Phe Gly Val Ala Gly Gln Leu<br>                      160                      165                      170 | 651 |
| aca gat aca atg gca aaa cgc aat act gta ata gga act cca ttt tgg<br>Thr Asp Thr Met Ala Lys Arg Asn Thr Val Ile Gly Thr Pro Phe Trp<br>                      175                      180                      185 | 699 |
| atg gct cct gag gtg att caa gaa ata ggc tat aac tgt gtg gcc gac<br>Met Ala Pro Glu Val Ile Gln Glu Ile Gly Tyr Asn Cys Val Ala Asp<br>                      190                      195                      200 | 747 |
| atc tgg tcc ctt ggc att act tct ata gaa atg gct gaa gga aaa cct<br>Ile Trp Ser Leu Gly Ile Thr Ser Ile Glu Met Ala Glu Gly Lys Pro<br>205                      210                      215 | 795 |
| cct tat gct gat ata cat cca atg agg gct att ttt atg att ccc aca<br>Pro Tyr Ala Asp Ile His Pro Met Arg Ala Ile Phe Met Ile Pro Thr<br>220                      225                      230                      235 | 843 |
| aat cca cca cca aca ttc aga aag cca gaa ctt tgg tcc gat gat ttc<br>Asn Pro Pro Pro Thr Phe Arg Lys Pro Glu Leu Trp Ser Asp Asp Phe<br>                      240                      245                      250 | 891 |
| acc gat ttt gtt aaa aag tgt ttg gtg aag aat cct gag cag aga gct<br>Thr Asp Phe Val Lys Lys Cys Leu Val Lys Asn Pro Glu Gln Arg Ala<br>                      255                      260                      265 | 939 |
| act gca aca caa ctt tta cag cat cct ttt atc aag aat gcc aaa cct<br>Thr Ala Thr Gln Leu Leu Gln His Pro Phe Ile Lys Asn Ala Lys Pro<br>270                      275                      280 | 987 |
| gta tca ata tta aga gac ctg atc aca gaa gct atg gag atc aaa gct<br>Val Ser Ile Leu Arg Asp Leu Ile Thr Glu Ala Met Glu Ile Lys Ala<br>285                      290                      295 | 1035 |
| aaa aga cat gac gaa cag caa cga gaa ttg gaa gag gaa gaa gaa aat<br>Lys Arg His Asp Glu Gln Gln Arg Glu Leu Glu Glu Glu Glu Glu Asn<br>300                      305                      310                      315 | 1083 |
| tcg gat gaa gat gag ctg gat tcc cac acc atg gtg aag act agt gtg<br>Ser Asp Glu Asp Glu Leu Asp Ser His Thr Met Val Lys Thr Ser Val<br>                      320                      325                      330 | 1131 |
| gga gag tgt ggc acc atg cgg gcc aca agc acg atg agt gaa ggg gcc<br>Gly Glu Cys Gly Thr Met Arg Ala Thr Ser Thr Met Ser Glu Gly Ala<br>                      335                      340                      345 | 1179 |
| cag acc atg att gaa cat aat agc acg atg ttg gaa tcc gac ttg ggg<br>Gln Thr Met Ile Glu His Asn Ser Thr Met Leu Glu Ser Asp Leu Gly<br>350                      355                      360 | 1227 |
| acc atg gtg ata aac agt gag gat gag gaa gaa gaa gat gga act atg<br>Thr Met Val Ile Asn Ser Glu Asp Glu Glu Glu Glu Asp Gly Thr Met | 1275 |

|   |   |   |   |   |   |   |   |   |   |   |   |   |   |   |   |      |
|---|---|---|---|---|---|---|---|---|---|---|---|---|---|---|---|------|
| 365 | | | 370 | | | | 375 | | | | | | | | | |
| aaa | aga | aat | gca | acc | tca | cca | caa | gta | caa | aga | cca | tct | ttc | atg | gac | 1323 |
| Lys | Arg | Asn | Ala | Thr | Ser | Pro | Gln | Val | Gln | Arg | Pro | Ser | Phe | Met | Asp | |
| 380 | | | | | 385 | | | | | 390 | | | | | 395 | |
| tac | ttt | gat | aag | caa | gac | ttc | aag | aat | aag | agt | cac | gaa | aac | tgt | aat | 1371 |
| Tyr | Phe | Asp | Lys | Gln | Asp | Phe | Lys | Asn | Lys | Ser | His | Glu | Asn | Cys | Asn | |
| | | | | 400 | | | | | 405 | | | | | 410 | | |
| cag | aac | atg | cat | gaa | ccc | ttc | cct | atg | tcc | aaa | aac | gtt | ttt | cct | gat | 1419 |
| Gln | Asn | Met | His | Glu | Pro | Phe | Pro | Met | Ser | Lys | Asn | Val | Phe | Pro | Asp | |
| | | | 415 | | | | | 420 | | | | | 425 | | | |
| aac | tgg | aaa | gtt | cct | caa | gat | gga | gac | ttt | gac | ttt | ttg | aaa | aat | cta | 1467 |
| Asn | Trp | Lys | Val | Pro | Gln | Asp | Gly | Asp | Phe | Asp | Phe | Leu | Lys | Asn | Leu | |
| | | 430 | | | | | 435 | | | | | 440 | | | | |
| agt | tta | gaa | gaa | cta | cag | atg | cgg | tta | aaa | gca | ctg | gac | ccc | atg | atg | 1515 |
| Ser | Leu | Glu | Glu | Leu | Gln | Met | Arg | Leu | Lys | Ala | Leu | Asp | Pro | Met | Met | |
| | 445 | | | | | 450 | | | | | 455 | | | | | |
| gaa | cgg | gag | ata | gaa | gaa | ctt | cgt | cag | aga | tac | act | gcg | aaa | aga | cag | 1563 |
| Glu | Arg | Glu | Ile | Glu | Glu | Leu | Arg | Gln | Arg | Tyr | Thr | Ala | Lys | Arg | Gln | |
| 460 | | | | | 465 | | | | | 470 | | | | | 475 | |
| ccc | att | ctg | gat | gcg | atg | gat | gca | aag | aaa | aga | agg | cag | caa | aac | ttt | 1611 |
| Pro | Ile | Leu | Asp | Ala | Met | Asp | Ala | Lys | Lys | Arg | Arg | Gln | Gln | Asn | Phe | |
| | | | | 480 | | | | | 485 | | | | | 490 | | |

| | |
|---|---|
| tga gtctaatttc ctctctgttt ttaactattc tggagaccaa gaaaccacta | 1664 |
| ggaattgaag gaatatttgg atattttaa tcctaagatt ttgccctaca attaggcaga | 1724 |
| ggtcaaaaag tgacaatggt acatgcccag gtaaattccc aaaaggcaga attgacagtt | 1784 |
| gtatctgctg tgcattcact ctaagatgag gagaacaaaa gaagtgtatt ctcttgttct | 1844 |
| gtcagctgca taccagtaat aaaactgtta tgaaatggat tttcaaggtc tctaaacctt | 1904 |
| gaaaatccaa aggctattgt tgcattgtac agcactgaaa gggctttatg ttacaatatt | 1964 |
| ctttattcct atctagtata ctaggctatt tattgtcccc ttaggtaaac ttatttattt | 2024 |
| atgctatttt ggctttgttt catttttttaa ggacaagatc aggatagctt tggtgaaggt | 2084 |
| agggtcatat taatatgatg ataatgtgca accaatttat actttctgca gggagctatg | 2144 |
| gggtacattc cttgatttcc aggatagttt ttcaaatagg aaagcaataa tggcagtagt | 2204 |
| tctcaaatgg gctaggcctt ttttatattg aagcaataat tccatttta cccttttgaaa | 2264 |
| ttttgttttt tgattttttg atgttttggta caaatagaac tatatatatt taggtaaaat | 2324 |
| agatctatcg tgtttaaaac caaagaaatc aatggaaccc ttgcacaaaa aagtgtgata | 2384 |
| aatatttta aataaaaact taatacaaat gtaatttgtt aatattgttt catgttttat | 2444 |
| gtgtagatct aatagctgaa ctgattcaaa ctgtaataag ctcatcaatt tcatttctat | 2504 |
| gaaaatgtgc tctgttgtca caggatgttt ctgttgattt tattcatttc ctgggaattg | 2564 |
| gtaaacatca tgttcctgat gataacccag tagcaaaaac atttgtactg agtggtacaa | 2624 |
| gccttgggga ctgaaaaaaa aaaaagatta aaaccattaa aaagaaactc atttttacgc | 2684 |
| tgaatgaaca tttatatgat tgcattggga ccagtcattt cctaagctac atatggccat | 2744 |
| cttgacagtg tttttttcttt tgtgtgttta attattatgt gtaaatcata aagcaaata | 2804 |
| aatttcactg tgccac | 2820 |

<210> SEQ ID NO 4
<211> LENGTH: 491
<212> TYPE: PRT
<213> ORGANISM: Homo sapiens

<400> SEQUENCE: 4

```
Met Gln Pro Pro Ala Pro Lys Ser Lys Leu Lys Leu Ser Glu
 1               5                  10                  15

Asp Ser Leu Thr Lys Gln Pro Glu Glu Val Phe Asp Val Leu Glu Lys
                20                  25                  30

Leu Gly Glu Gly Ser Tyr Gly Ser Val Phe Lys Ala Ile His Lys Glu
                35                  40                  45

Ser Gly Gln Val Val Ala Ile Lys Gln Val Pro Val Glu Ser Asp Leu
                50                  55                  60

Gln Glu Ile Ile Lys Glu Ile Ser Ile Met Gln Gln Cys Asp Ser Pro
 65                  70                  75                  80

Tyr Val Val Lys Tyr Tyr Gly Ser Tyr Phe Lys Asn Thr Asp Leu Trp
                    85                  90                  95

Ile Val Met Glu Tyr Cys Gly Ala Gly Ser Val Ser Asp Ile Ile Arg
                    100                 105                 110

Leu Arg Asn Lys Thr Leu Ile Glu Asp Glu Ile Ala Thr Ile Leu Lys
                    115                 120                 125

Ser Thr Leu Lys Gly Leu Glu Tyr Leu His Phe Met Arg Lys Ile His
130                 135                 140

Arg Asp Ile Lys Ala Gly Asn Ile Leu Leu Asn Thr Glu Gly His Ala
145                 150                 155                 160

Lys Leu Ala Asp Phe Gly Val Ala Gly Gln Leu Thr Asp Thr Met Ala
                    165                 170                 175

Lys Arg Asn Thr Val Ile Gly Thr Pro Phe Trp Met Ala Pro Glu Val
                180                     185                 190

Ile Gln Glu Ile Gly Tyr Asn Cys Val Ala Asp Ile Trp Ser Leu Gly
                195                     200                 205

Ile Thr Ser Ile Glu Met Ala Glu Gly Lys Pro Pro Tyr Ala Asp Ile
210                     215                 220

His Pro Met Arg Ala Ile Phe Met Ile Pro Thr Asn Pro Pro Pro Thr
225                 230                     235                 240

Phe Arg Lys Pro Glu Leu Trp Ser Asp Phe Thr Asp Phe Val Lys
                    245                 250                 255

Lys Cys Leu Val Lys Asn Pro Glu Gln Arg Ala Thr Ala Thr Gln Leu
                    260                 265                 270

Leu Gln His Pro Phe Ile Lys Asn Ala Lys Pro Val Ser Ile Leu Arg
                275                     280                 285

Asp Leu Ile Thr Glu Ala Met Glu Ile Lys Ala Lys Arg His Asp Glu
                290                     295                 300

Gln Gln Arg Glu Leu Glu Glu Glu Glu Asn Ser Asp Glu Asp Glu
305                 310                     315                 320

Leu Asp Ser His Thr Met Val Lys Thr Ser Val Gly Glu Cys Gly Thr
                    325                 330                 335

Met Arg Ala Thr Ser Thr Met Ser Glu Gly Ala Gln Thr Met Ile Glu
                340                     345                 350

His Asn Ser Thr Met Leu Glu Ser Asp Leu Gly Thr Met Val Ile Asn
                355                     360                 365

Ser Glu Asp Glu Glu Glu Asp Gly Thr Met Lys Arg Asn Ala Thr
                370                     375                 380

Ser Pro Gln Val Gln Arg Pro Ser Phe Met Asp Tyr Phe Asp Lys Gln
385                 390                     395                 400

Asp Phe Lys Asn Lys Ser His Glu Asn Cys Asn Gln Asn Met His Glu
                    405                 410                 415
```

```
-continued

Pro Phe Pro Met Ser Lys Asn Val Phe Pro Asp Asn Trp Lys Val Pro
            420             425             430

Gln Asp Gly Asp Phe Asp Phe Leu Lys Asn Leu Ser Leu Glu Glu Leu
            435             440             445

Gln Met Arg Leu Lys Ala Leu Asp Pro Met Met Glu Arg Glu Ile Glu
        450             455             460

Glu Leu Arg Gln Arg Tyr Thr Ala Lys Arg Gln Pro Ile Leu Asp Ala
465             470             475             480

Met Asp Ala Lys Lys Arg Arg Gln Gln Asn Phe
                485             490
```